(12) United States Patent
Kishi

(10) Patent No.: US 9,050,727 B2
(45) Date of Patent: Jun. 9, 2015

(54) MASTER OPERATION INPUT DEVICE AND MASTER-SLAVE MANIPULATOR

(75) Inventor: Kosuke Kishi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 746 days.

(21) Appl. No.: 13/306,154

(22) Filed: Nov. 29, 2011

(65) Prior Publication Data

US 2012/0143353 A1 Jun. 7, 2012

(30) Foreign Application Priority Data

Nov. 30, 2010 (JP) ................................. 2010-267522

(51) Int. Cl.
*G06F 19/00* (2011.01)
*B25J 9/16* (2006.01)
(Continued)

(52) U.S. Cl.
CPC ........... *B25J 9/1689* (2013.01); *A61B 19/2203* (2013.01); *A61B 2019/2223* (2013.01);
(Continued)

(58) Field of Classification Search
CPC .................. A61B 2019/2223; A61B 19/2203; A61B 19/22; A61B 2019/223; A61B 2019/2234; A61B 2019/265; A61B 2017/00477; A61B 2019/2296; A61B 19/5212; A61B 2019/2292; A61B 2019/2242; A61B 2019/464; A61B 19/52; A61B 1/00149; A61B 2019/502; A61B 2017/00703; A61B 2019/2246; A61B 2019/2269; A61B 1/00188; A61B 2017/00207; A61B 2019/2273; A61B 2019/5265; A61B 17/00234; A61B 18/1445; A61B 2017/2927; A61B 2017/2932; A61B 2017/2939; A61B 2018/00982; A61B 2019/2276; A61B 2019/5251; A61B 2560/0276; A61B 5/14532; A61B 5/6823; A61B 5/742; B25J 9/1689; B25J 15/0009; B25J 13/02; B25J 3/04; B25J 9/1612; B25J 13/08; B25J 3/00; B25J 9/1615; B25J 19/023; B25J 9/161; B25J 9/1692; B25J 13/025; B25J 13/084; B25J 13/089; B25J 15/103; B25J 17/0216; B25J 17/0266; B25J 19/0016; B25J 19/04; B25J 5/007; B25J 9/00; B25J 9/104; B25J 9/16
USPC .................................................... 700/245–264
See application file for complete search history.

(56) References Cited

U.S. PATENT DOCUMENTS 5,339,799 A * 8/1994 Kami et al. ................... 600/117
5,451,924 A * 9/1995 Massimino et al. ....... 340/407.1
(Continued)

FOREIGN PATENT DOCUMENTS

| CN | 1864938 A | 11/2006 |
| EP | 1 724 071 A1 | 11/2006 |

(Continued)

OTHER PUBLICATIONS

English Translation of International Search Report PCT/JP2011/077072 dated Jan. 17, 2012.
(Continued)

*Primary Examiner* — Bhavesh V Amin
(74) *Attorney, Agent, or Firm* — Scully, Scott, Murphy & Presser, PC

(57) ABSTRACT

A master operation input device operates a slave manipulator provided with joints adapted to multiple degrees of freedom. The master operation input device includes a grip portion and a first operation portion. The grip portion is variable in position and orientation while being gripped by an operator. The grip portion is configured to give command values regarding the position and orientation of a distal end of the slave manipulator in accordance with the variation in position and orientation. The distal end is the farthest end when the slave manipulator is viewed from a fixed end thereof. The first operation portion is located to be operable by a fingertip of the operator when the grip portion is gripped. The first operation portion is operable independently of the grip portion.

14 Claims, 20 Drawing Sheets

(51) Int. Cl.
*A61B 19/00* (2006.01)
*B25J 3/04* (2006.01)
*B25J 13/02* (2006.01)

(52) U.S. Cl.
CPC . *A61B2019/4857* (2013.01); *A61B 2560/0487* (2013.01); *B25J 3/04* (2013.01); *B25J 13/02* (2013.01)

(56) References Cited

U.S. PATENT DOCUMENTS

| | | | |
|---|---|---|---|
| 5,587,937 A * | 12/1996 | Massie et al. | 703/7 |
| 5,619,180 A * | 4/1997 | Massimino et al. | 340/407.1 |
| 5,649,955 A * | 7/1997 | Hashimoto et al. | 606/205 |
| 5,792,165 A * | 8/1998 | Klieman et al. | 606/170 |
| 6,077,287 A * | 6/2000 | Taylor et al. | 606/170 |
| 6,424,885 B1 * | 7/2002 | Niemeyer et al. | 700/245 |
| 6,435,794 B1 * | 8/2002 | Springer | 414/5 |
| 6,889,116 B2 * | 5/2005 | Jinno | 700/245 |
| 7,043,338 B2 * | 5/2006 | Jinno | 700/245 |
| 7,454,268 B2 * | 11/2008 | Jinno | 700/245 |
| 8,157,817 B2 * | 4/2012 | Bonadio et al. | 606/148 |
| 8,277,443 B2 * | 10/2012 | Jinno | 606/1 |
| 2002/0040217 A1 | 4/2002 | Jinno | |
| 2008/0091072 A1 * | 4/2008 | Omori et al. | 600/131 |
| 2008/0167662 A1 * | 7/2008 | Kurtz | 606/130 |
| 2009/0112229 A1 * | 4/2009 | Omori et al. | 606/130 |
| 2009/0132088 A1 * | 5/2009 | Taitler | 700/264 |
| 2011/0118752 A1 * | 5/2011 | Itkowitz et al. | 606/130 |
| 2011/0118753 A1 * | 5/2011 | Itkowitz et al. | 606/130 |
| 2012/0090423 A1 * | 4/2012 | Helmer et al. | 74/491 |

FOREIGN PATENT DOCUMENTS

| | | |
|---|---|---|
| JP | 5-228854 | 9/1993 |
| JP | 7-246578 A | 9/1995 |
| JP | 2002-102248 A | 4/2002 |
| JP | 2003-340752 A | 12/2003 |
| JP | 3712693 | 8/2005 |
| JP | 2008-173724 A | 7/2008 |
| JP | 2009-34813 A | 2/2009 |

OTHER PUBLICATIONS

English-language Abstract of Japanese Patent Publication No. 2003-340752, dated Dec. 2, 2003.
English translation of International Preliminary Report on Patentability together with the Written Opinion dated Jun. 13, 2013 received in related International Application No. PCT/JP2011/077072.
Extended Supplementary European Search Report dated Dec. 6, 2013 from related European Application No. 11 84 5490.9.
Chinese Office Action dated Sep. 3, 2014 from related Chinese Application No. 201180057730.X, together with an English language translation.

* cited by examiner

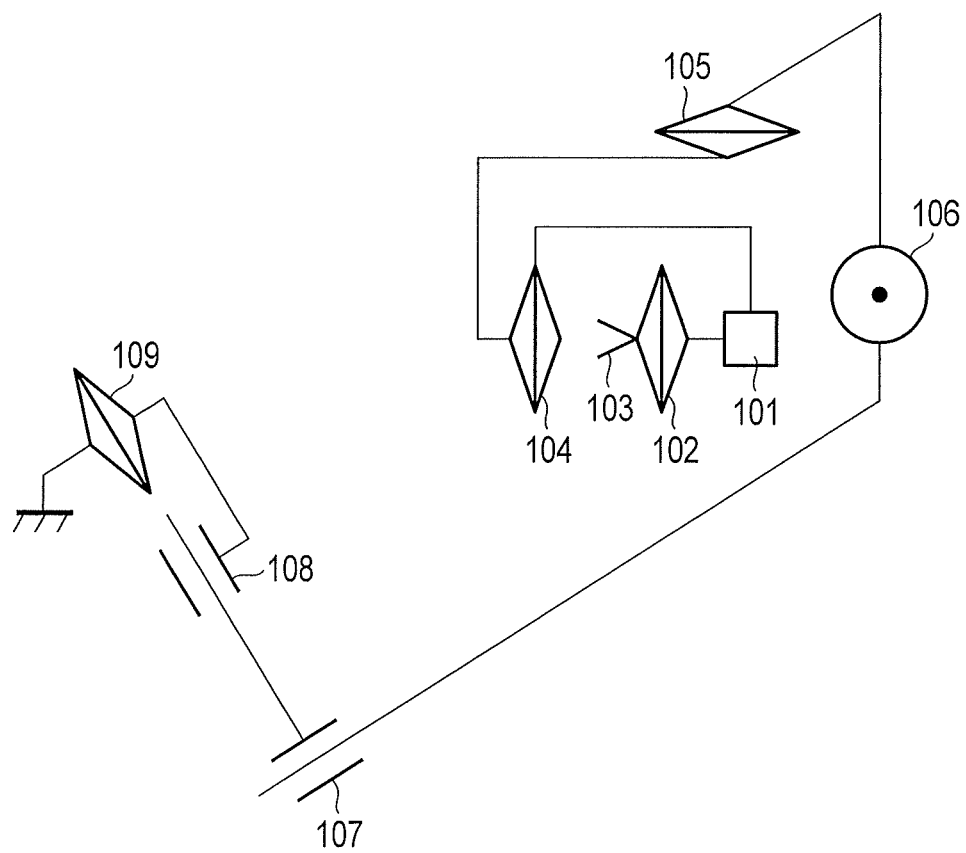
F I G. 3

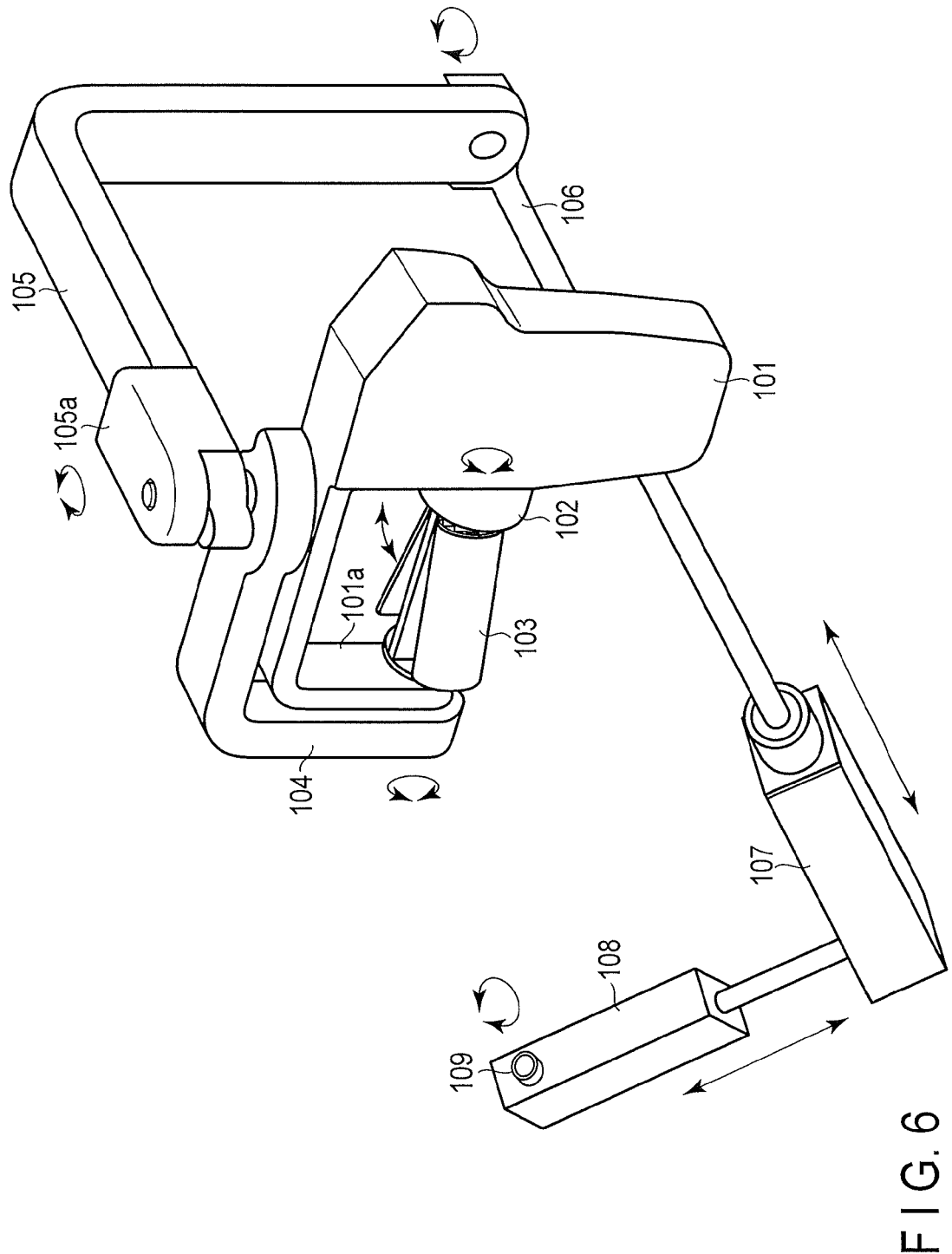
F I G. 6

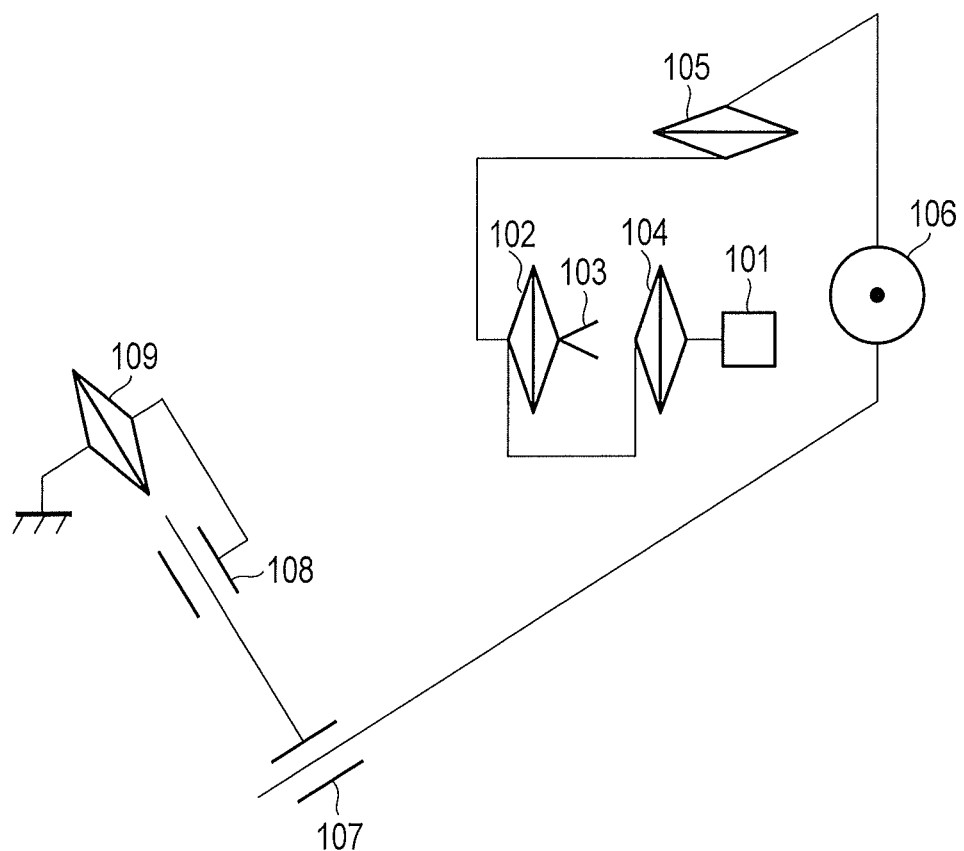
F I G. 7

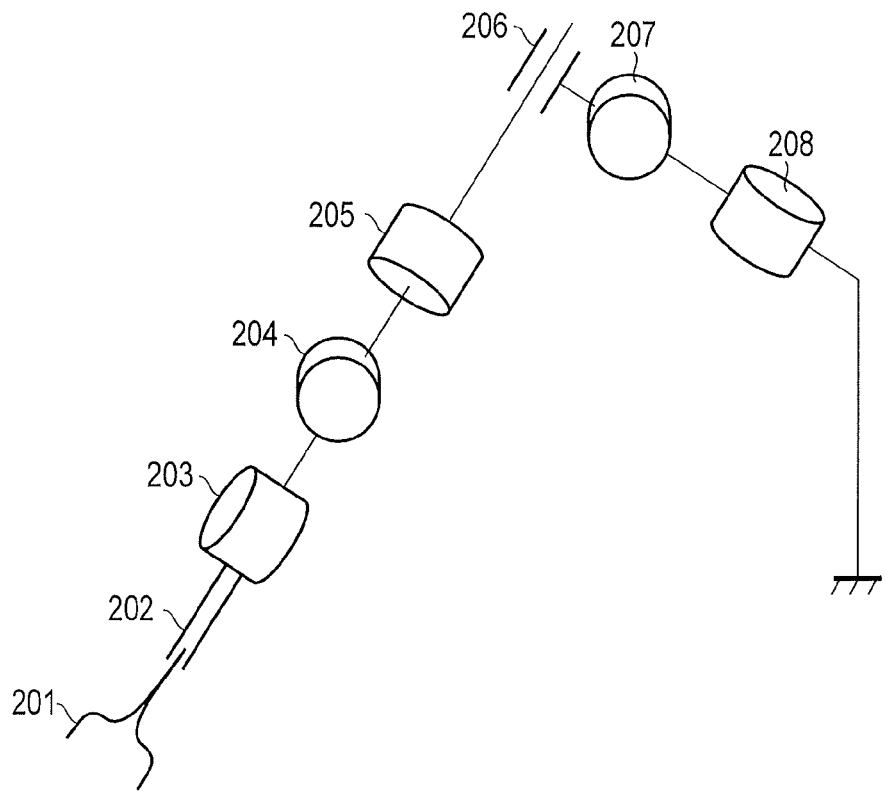
F I G. 10A
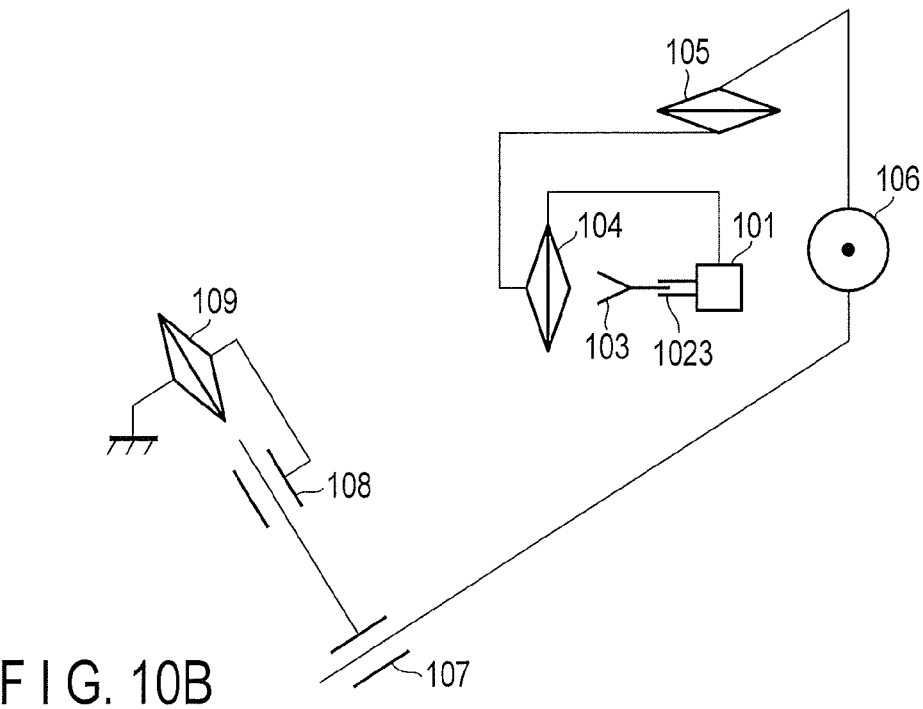
F I G. 10B

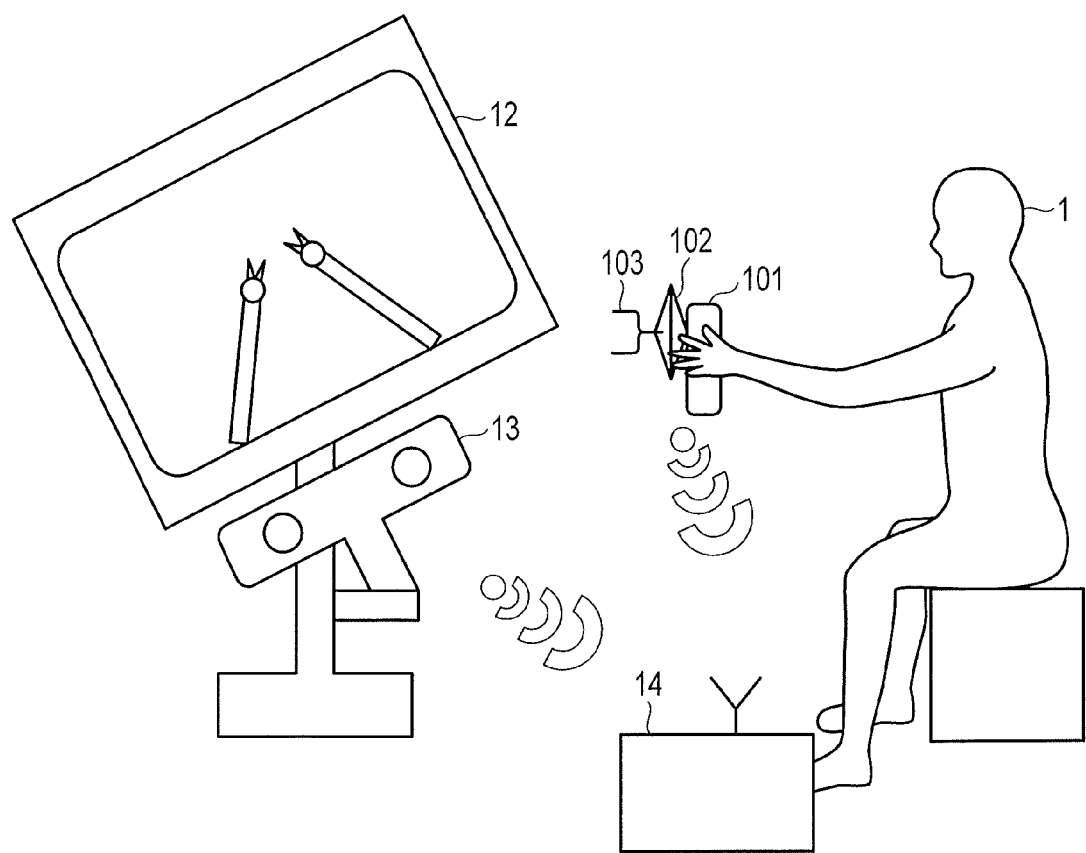
F I G. 12

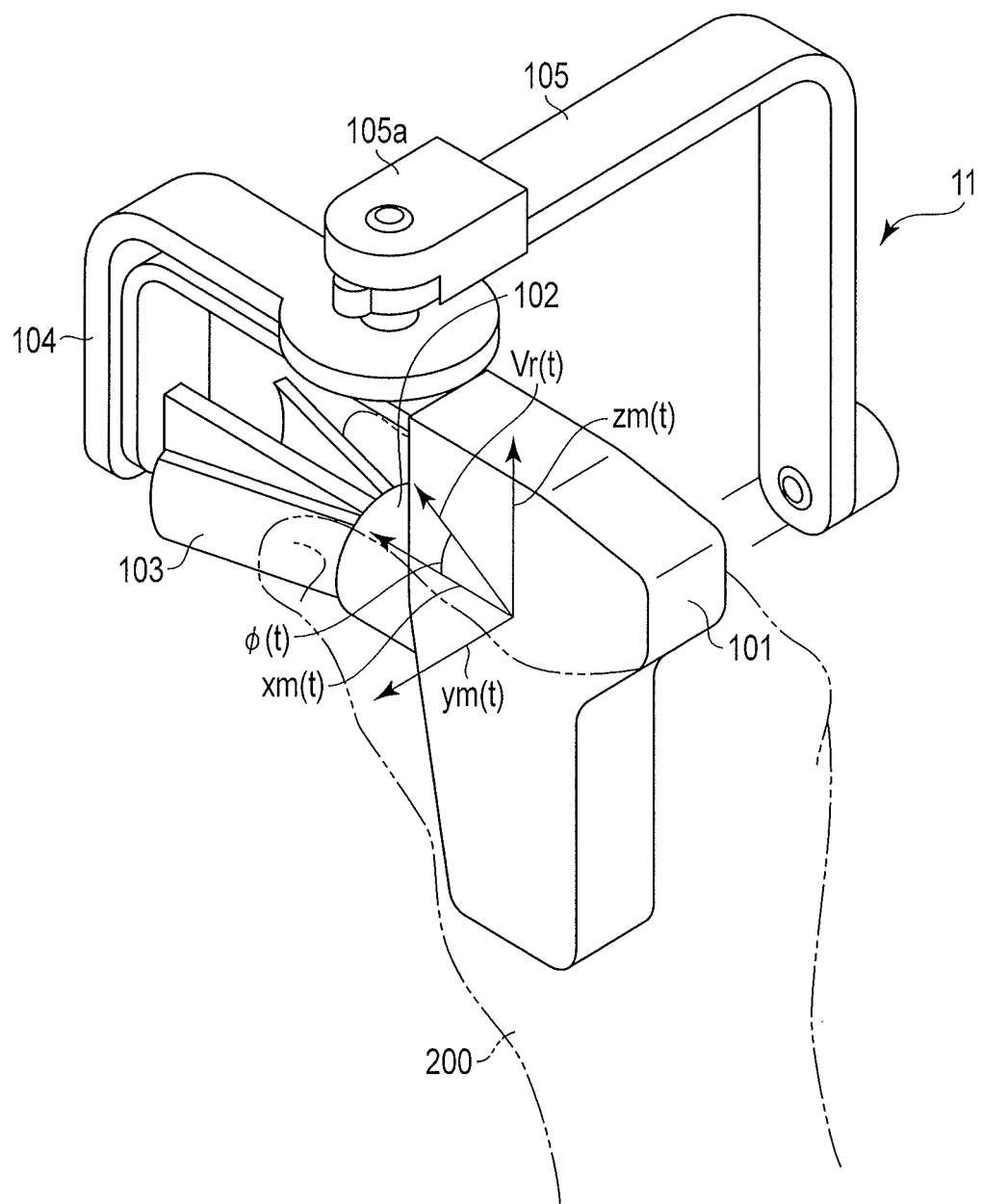
F I G. 13C

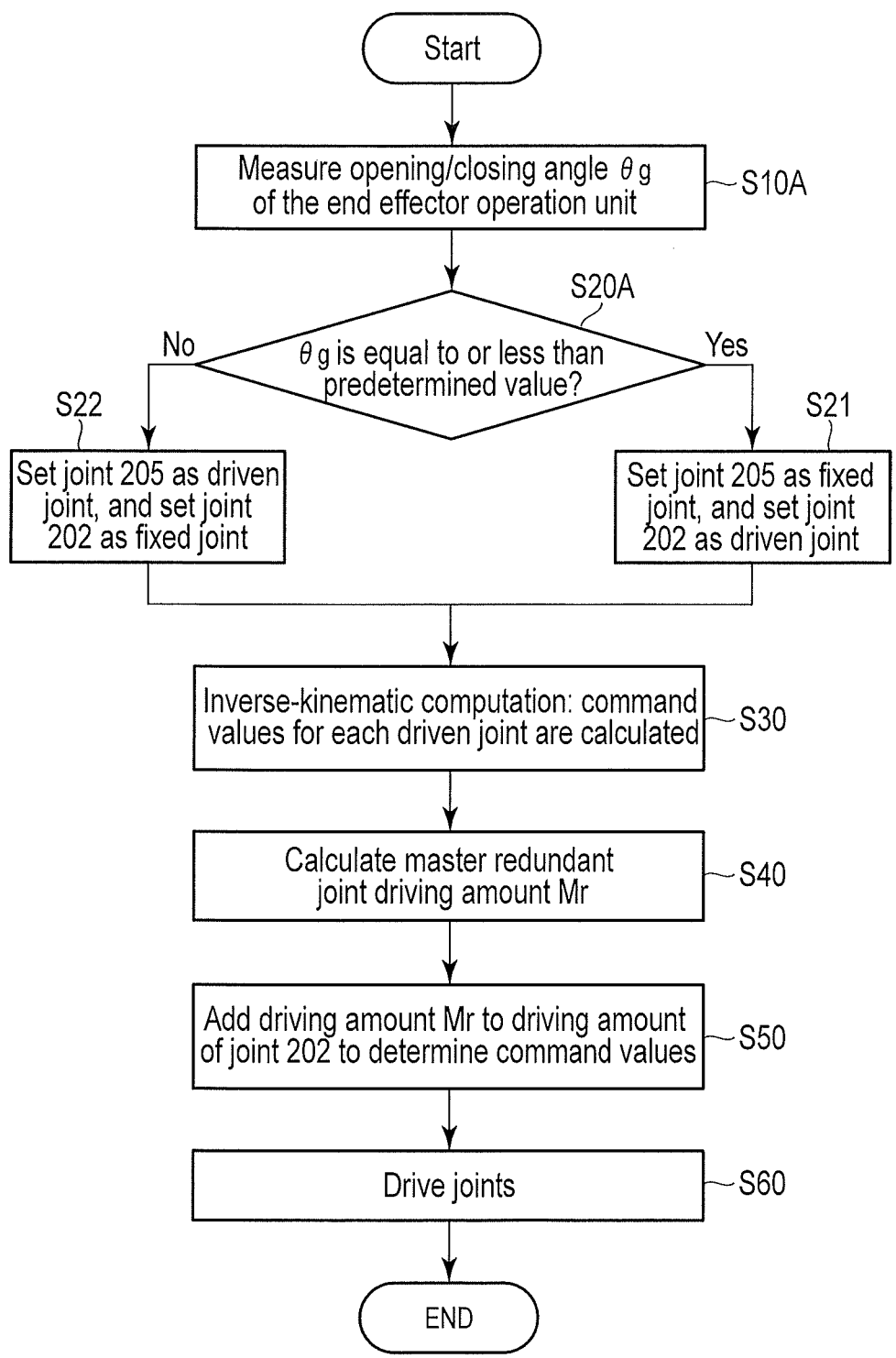
F I G. 16

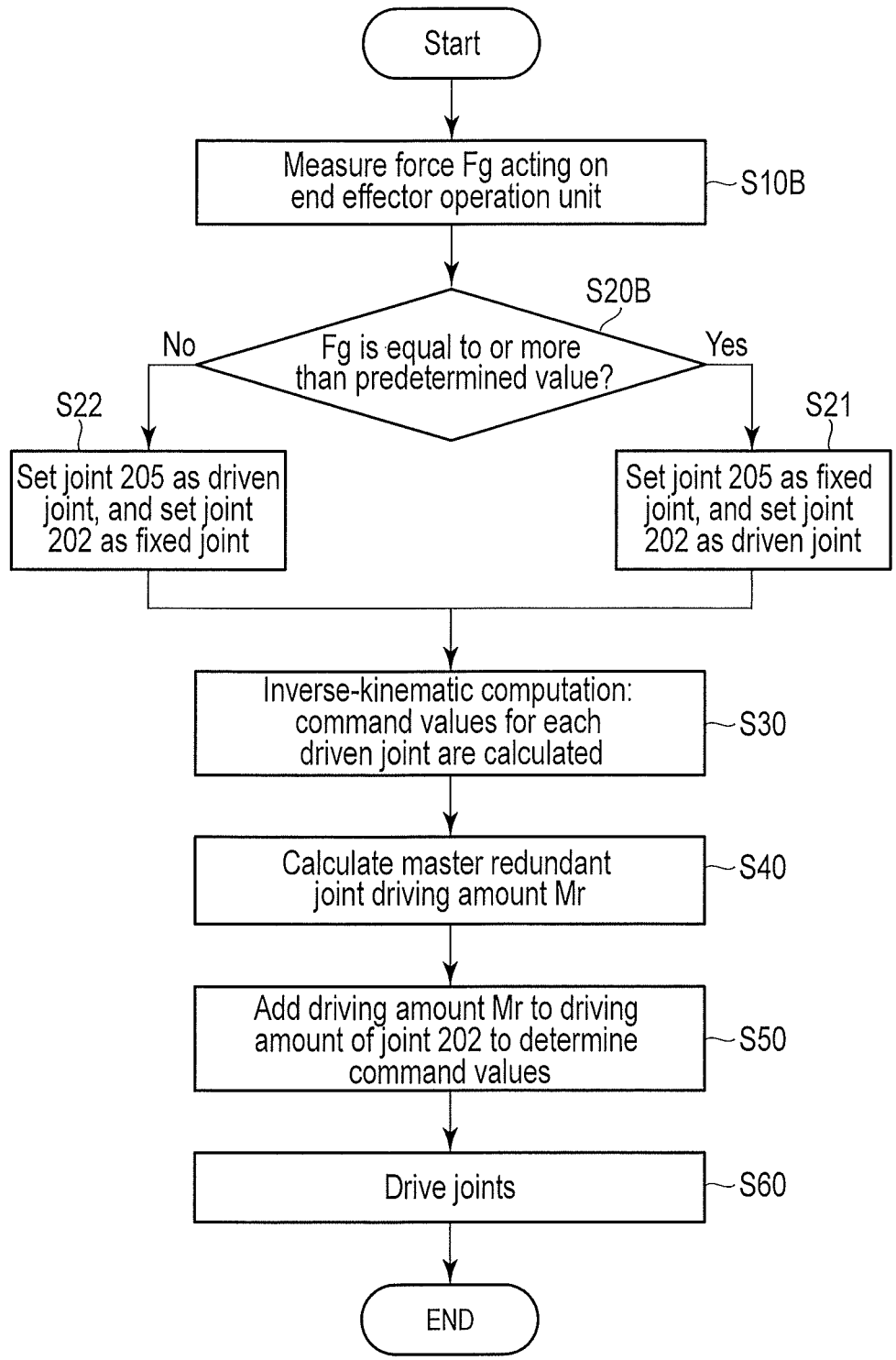
F I G. 18

MASTER OPERATION INPUT DEVICE AND MASTER-SLAVE MANIPULATOR

CROSS-REFERENCE TO RELATED APPLICATIONS

This application is based upon and claims the benefit of priority from the prior Japanese Patent Application No. 2010-267522, filed Nov. 30, 2010, the entire contents of which are incorporated herein by reference.

BACKGROUND OF THE INVENTION

1. Field of the Invention

The present invention relates to a master operation input device for remote control of a slave manipulator, and a master-slave manipulator comprising the master operation input device.

2. Description of the Related Art

Recently, in order to reduce manpower in medical facilities, medical procedures using robots have been under study. Particularly in the field of surgery, various suggestions have been made regarding a manipulator system that uses a manipulator having multidegree-of-freedom (multiarticular) arms to operate on a patient. In connection with such manipulator systems, there has been known a manipulator system (master-slave manipulator) in which a manipulator (slave manipulator) that comes into direct contact with a body cavity of a patient can be remotely operated on by a master operation input device. Recently, there has been also known a master-slave manipulator in which a slave arm of a slave manipulator has seven or more degrees of freedom (three degrees of freedom in position+three degrees of freedom in orientation+redundant degree of freedom).

In general, a slave arm having seven or more degrees of freedom requires complex inverse-kinematic computation to calculate the driving amount of each joint of the slave arm if six or less command values can be input from the master operation input device. One suggestion to avoid such complex computation has been suggested in, for example, Jpn. Pat. Appln. KOKAI Publication No. 5-228854. According to Jpn. Pat. Appln. KOKAI Publication No. 5-228854, an operation unit such as a switch or a dial is additionally provided in a master arm (master operation input device) that allows command values for six degrees of freedom to be input by the operation of a handle, thereby enabling command values corresponding to seven degrees of freedom to be input with one hand.

BRIEF SUMMARY OF THE INVENTION

According to a first aspect of the invention, there is provided a master operation input device to operate a slave manipulator provided with joints adapted to multiple degrees of freedom, the master operation input device comprising: a grip portion which is variable in position and orientation while being gripped by an operator, the grip portion being configured to give command values regarding the position and orientation of a distal end of the slave manipulator in accordance with the variation in position and orientation, the distal end being the farthest end when the slave manipulator is viewed from a fixed end thereof; and a first operation portion which is located to be operable by a fingertip of the operator when the grip portion is gripped, the first operation portion being operable independently of the grip portion.

According to a second aspect of the invention, there is provided a master-slave manipulator comprising: a slave manipulator provided with joints adapted to multiple degrees of freedom; the master operation input device according to the first aspect; and a control unit configured to calculate a driving amount of each joint of the slave manipulator from the command values regarding the position and orientation and from a command value regarding a driving amount to drive the joint at the distal end of the slave manipulator, the control unit driving each joint of the slave manipulator in accordance with a calculation result of the driving amount.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 3 is a schematic diagram of the operation unit having the configuration shown in FIG. 2;

FIG. 6 is a diagram showing the configuration of an operation unit according to a modification in which a first rolling joint has a double-shaft structure;

FIG. 7 is a schematic diagram of the operation unit having the configuration shown in FIG. 6;

FIG. 10A is a diagram showing the structure of a slave arm according to a modification in which a joint provided in a grip portion is a translation joint;

FIG. 10B is a diagram showing the structure of a master operation input device according to the modification in which the joint provided in the grip portion is a translation joint;

FIG. 12 is a diagram showing an example of a wireless operation unit;

FIG. 13C is a diagram for explanation of move of an operation unit;

FIG. 16 is a flowchart showing the flow of the driving of the joints of the slave arm in a second embodiment of the invention;

FIG. 18 is a flowchart showing the flow of the driving of the joints of the slave arm in a third embodiment of the invention.

DETAILED DESCRIPTION OF THE INVENTION

An embodiment according to the present invention will hereinafter be described with reference to the drawings.

Figure 1:
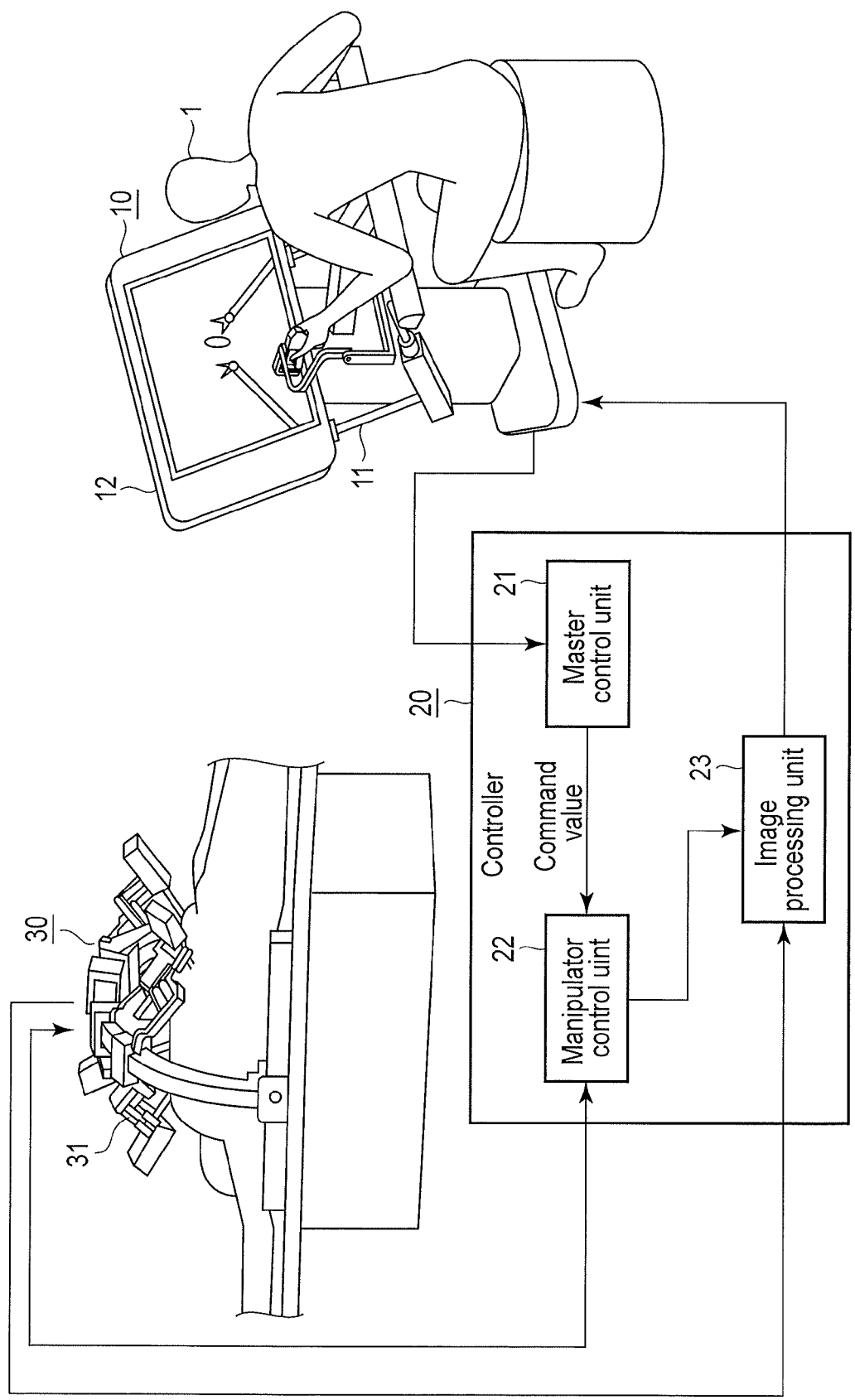
FIG. 1 is a diagram showing the overall configuration of a master-slave manipulator according to one embodiment of the present invention.

FIG. 1 is a diagram showing the overall configuration of an example of a master-slave manipulator according to one embodiment of the present invention. As shown in FIG. 1, the master-slave manipulator according to the present embodiment comprises a master operation input device 10, a controller 20, and a slave manipulator 30.

The master operation input device 10 functions as a master in the present master-slave manipulator, and comprises an operation unit 11 and a display unit 12.

The operation unit 11 is fixed to, for example, the display unit 12 of the master operation input device 10, and when operated by an operator, outputs an operation signal for operating the slave manipulator 30.

Figure 2:
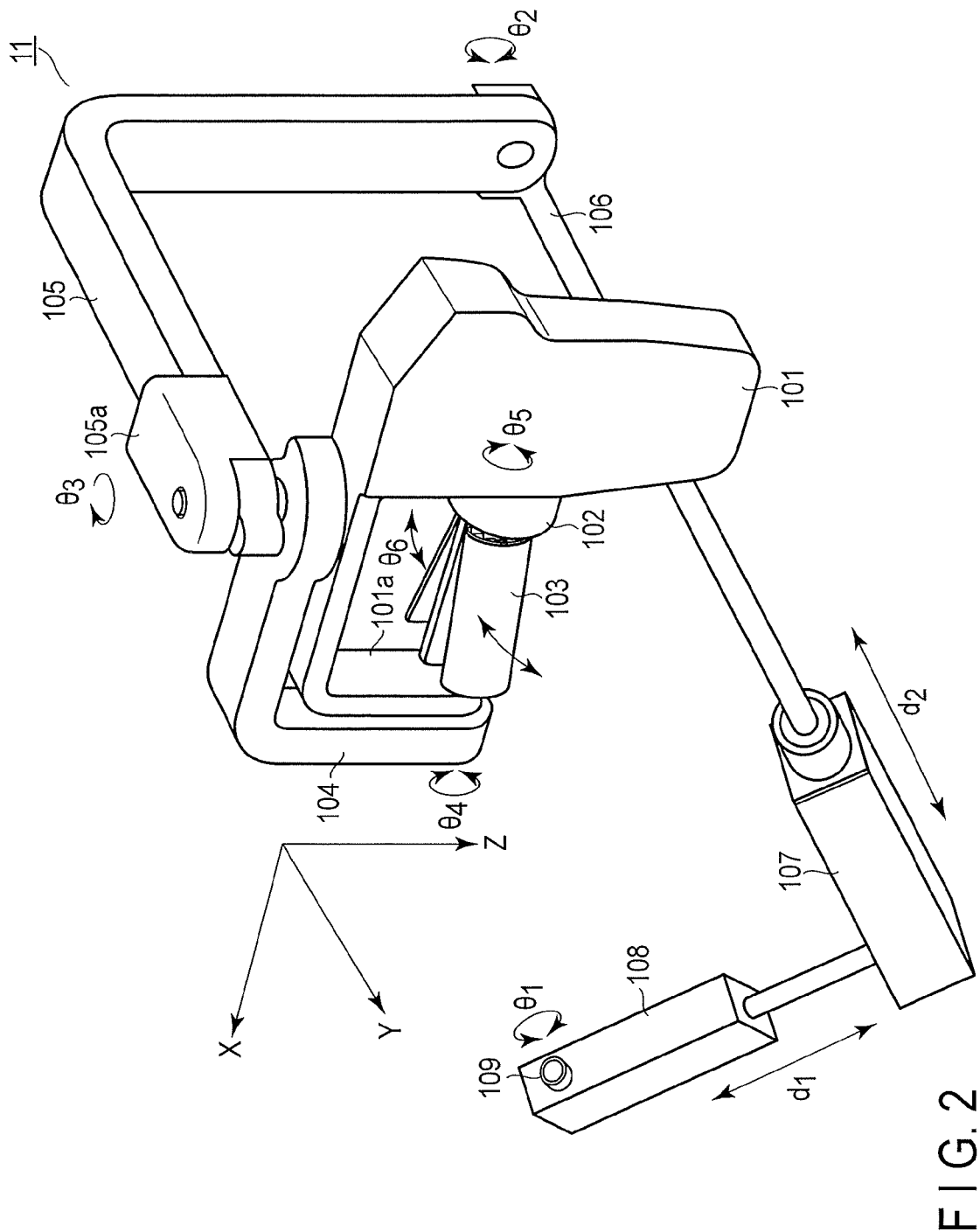
FIG. 2 is a diagram showing the configuration of an operation unit of a master operation input device according to the embodiment.

FIG. 2 is a diagram showing the configuration of the operation unit 11 of the master operation input device 10 according to the present embodiment. FIG. 3 is a schematic diagram of the operation unit 11 having the configuration shown in FIG. 2. Here, FIG. 2 shows the configuration of the right-handed operation unit. The configuration of a left-handed operation unit is only inverted horizontally relative to the configuration of the right-handed operation unit, and is substantially similar to the configuration shown in FIG. 2.

As shown in FIG. 2, the operation unit 11 has a grip portion 101. The grip portion 101 is a portion to be gripped by an operator 1 with his/her hand. The grip portion 101 is supported movably in the directions of three orthogonal axes (X-, Y-, and Z-axes shown in FIG. 2) and in the directions to rotate around the respective axes. Here, in FIG. 2, the X-axis is set so that the direction parallel to the ground to travel from the face of the operator 1 to the display unit 12 is a positive direction when the operator 1 operates the master operation input device 10 as shown in FIG. 1. The Y-axis is set along a direction parallel to the ground and perpendicular to the X-axis. The Z-axis is set along a direction perpendicular to the ground.

A first rolling joint 102 as an example of a first operation portion is pivotally fastened to the grip portion 101. In such a configuration, the first rolling joint 102 has its rotary shaft parallel to the X-axis shown in FIG. 2, and is configured to be able to be rotated by a fingertip when the operator 1 holds the grip portion 101 with his/her hand. An unshown position sensor (e.g., an encoder) is provided in the vicinity of the first rolling joint 102. When the first rolling joint 102 is rotated by the operator 1, a resultant driving amount (rotation amount) $\theta_5$ is detected by the position sensor. From this position sensor, an operation signal corresponding to the driving amount (rotation amount) $\theta_5$ of the first rolling joint 102 is input to a master control unit 21 of the controller 20. As will be described later, the operation signal of the first rolling joint 102 is a signal for providing a command value to give a direct command regarding the driving amount of a joint at the distal end of a slave arm 31 of the slave manipulator 30.

An end effector operation unit 103 as an example of a second operation portion is attached collinearly with the first rolling joint 102. That is, the first rolling joint 102 and the end effector operation unit 103 are operably attached independently of the position and orientation of the grip portion 101. The end effector operation unit 103 is configured to be able to be opened/closed with a fingertip when the operator 1 holds the grip portion 101 with his/her hand. An unshown position sensor (e.g., an encoder) is provided in the vicinity of the end effector operation unit 103. When the end effector operation unit 103 is opened/closed by the operator 1, a resultant opening/closing amount (opening/closing angle $\theta_6$) is detected by the position sensor. From this position sensor, an operation signal corresponding to the opening/closing amount $\theta_6$ of the end effector operation unit 103 is input to a master control unit 21 of the controller 20. As will be described later, the operation signal of the end effector operation unit 103 is a signal for providing a command value to give a direct command regarding the opening/closing amount of an end effector attached to a joint at the distal end of the slave arm 31 of the slave manipulator 30.

The grip portion 101 extends in the positive direction (a direction to depart from the operator 1 in FIG. 1) of the X-axis by the length of the first rolling joint 102 in the X-axis direction and by the length of the end effector operation unit 103 in the X-axis direction, thereby configuring a first link. The first link further extends in the positive direction (a direction toward the ground in FIG. 1) of the Z-axis. An extension 101a of the first link oriented in the positive direction of the Z-axis is pivotally fastened in a rotatable state to a second link 104 in a position collinear with the rotary shaft of the first rolling joint 102. An unshown position sensor (e.g., an encoder) is provided in the vicinity of a second rolling joint (having the same sign as the second link in FIG. 3) that comprises the extension 101a and the second link 104. When the second rolling joint is driven in response to the operation of the grip portion 101 by the operator 1, a resultant driving amount (rotation amount) $\theta_4$ is detected by the position sensor. From this position sensor, an operation signal corresponding to the driving amount $\theta_4$ of the second rolling joint is input to the master control unit 21 of the controller 20.

The second link 104 extends parallel to the extension 101a of the first link in the negative direction of the Z-axis and in the negative direction of the X-axis, and is thus pivotally fastened to a third link 105 in a rotatable state. A cover 105a is attached to the third link 105. The cover 105a prevents the fall of a rotary shaft in a yawing joint (having the same sign as the third link in FIG. 3) that comprises the second link 104 and the third link 105. An unshown position sensor (e.g., an encoder) is provided in the vicinity of the yawing joint that comprises the second link 104 and the third link 105. When the yawing joint is driven in response to the operation of the grip portion 101 by the operator 1, a resultant driving amount (rotation amount) $\theta_3$ is detected by the position sensor. From this position sensor, an operation signal corresponding to the driving amount $\theta_3$ of the yawing joint is input to the master control unit 21 of the controller 20.

The third link 105 extends in the negative direction of the Y-axis (a rightward direction in FIG. 1), and further extends in the positive direction of the Z-axis, and is thus pivotally fastened to a fourth link 106 in a rotatable state. An unshown position sensor (e.g., an encoder) is provided in the vicinity of a pitch joint (having the same sign as the fourth link in FIG. 3) that comprises the third link 105 and the fourth link 106. When the pitch joint is driven in response to the operation of the grip portion 101 by the operator 1, a resultant driving amount (rotation amount) $\theta_2$ is detected by the position sensor. From this position sensor, an operation signal corresponding to the driving amount $\theta_2$ of the pitch joint is input to the master control unit 21 of the controller 20.

The fourth link 106 is attached to a first translation joint 107. An unshown position sensor (e.g., an encoder) is provided in the vicinity of the first translation joint 107. When the first translation joint 107 is driven in response to the operation of the grip portion 101 by the operator 1, a resultant driving amount (translation amount) $d_2$ is detected by the position sensor. From this position sensor, an operation signal corresponding to the driving amount $d_2$ of the first translation joint 107 is input to the master control unit 21 of the controller 20.

A fifth link extends from the first translation joint 107 in a direction that intersects at right angles with the fourth link 106. The fifth link is attached to a second translation joint 108. An unshown position sensor (e.g., an encoder) is provided in the vicinity of the second translation joint 108. When the second translation joint 108 is driven in response to the operation of the grip portion 101 by the operator 1, a resultant driving amount (translation amount) $d_1$ is detected by the position sensor. From this position sensor, an operation signal corresponding to the driving amount $d_1$ of the second translation joint 108 is input to the master control unit 21 of the controller 20.

A rotary member 109 configured to be rotatable in a yawing direction is attached to the second translation joint 108. An unshown position sensor (e.g., an encoder) is provided in the vicinity of the rotary member 109. When the rotary member 109 is driven in response to the operation of the grip portion 101 by the operator 1, a resultant driving amount (rotation amount) $\theta_1$ is detected by the position sensor. From this position sensor, an operation signal corresponding to the driving amount $\theta_1$ of the rotary member 109 is input to the master control unit 21 of the controller 20.

Figure 4:
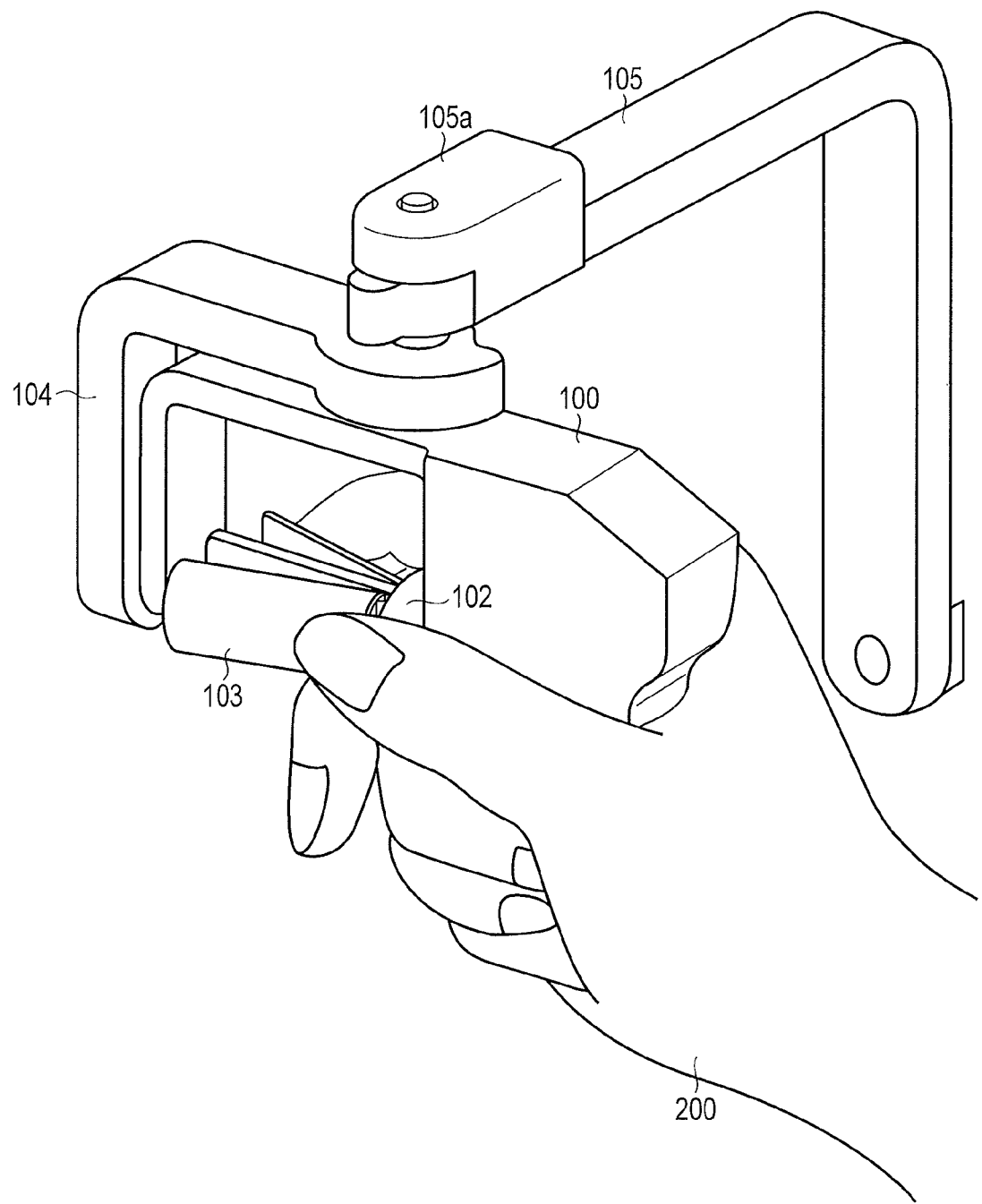
FIG. 4 is a diagram showing how the operation unit of the master operation input device is actually operated.

FIG. 4 shows how the operation unit 11 of the master operation input device 10 is actually operated. As shown in FIG. 4, the operator 1 changes the position and orientation of the grip portion 101 by the movement of the wrist, elbow, and shoulder while gripping the grip portion 101 with a hand 200. Each joint of the operation unit 11 is driven in response to the changes in the position and orientation of the grip portion 101. The driving amount of each joint is detected by the position sensor disposed in the vicinity of each joint, and an operation signal corresponding to each driving amount is input to the master control unit 21.

As shown in FIG. 4, in the present embodiment, the operator 1 can grip the grip portion 101 and at the same time operate the first rolling joint 102 and the end effector operation unit 103 with his/her fingertip. The operation amounts of the first rolling joint 102 and the end effector operation unit 103 are detected by the position sensors disposed in the vicinity of these units, and operation signals corresponding to the respective driving amounts are input to the master control unit 21.

According the configuration described above, the operation unit 11 inputs, to the master control unit 21 of the controller 20, the operation signals (+ the operation signal of the end effector) corresponding to seven degrees of freedom including six operation signals corresponding to the changes in the position and orientation of the grip portion 101 and the operation signal indicating the operation amount of the first rolling joint 102.

Here, the explanation continues returning to FIG. 1. The display unit 12 shown in FIG. 1 comprises, for example, a liquid crystal display, and displays an image in accordance with an image signal input from the controller 20. As will be described later, the image signal input from the controller 20 is provided by processing, in the controller 20, an image signal which is obtained via an electronic camera (electronic endoscope) attached to the slave arm 31. The image based on such an image signal is displayed on the display unit 12 so that the operator 1 of the master operation input device 10 can check an image of the end of the slave manipulator 30 located apart from the master operation input device 10.

The controller 20 comprises the master control unit 21, a manipulator control unit 22, and an image processing unit 23.

The master control unit 21 calculates command values for the position and orientation of the lend of the slave arm 31, for example, by inverse-kinematic computation in accordance with the operation signals from the master operation input device 10, and outputs the command values for the position and orientation to the manipulator control unit 22. The master control unit 21 also outputs, to the manipulator control unit 22, the operation signal for giving a command regarding the driving amount of the distal joint and the operation signal for giving a command regarding the driving amount of the end effector from the master operation input device 10.

In response to the command values for the position and orientation from the master control unit 21, the manipulator control unit 22 calculates, for example, by inverse-kinematic computation, the driving amount of each joint of the slave arm 31 necessary for the position and orientation of the end of the slave arm 31 to correspond to the command values. The manipulator control unit 22 then drives each joint of the slave arm 31 in accordance with the calculated driving amount. The manipulator control unit 22 also drives the joint at the distal end of the slave arm 31 and drives the end effector in response to the operation signal for giving a command regarding the driving amount of the distal joint and the operation signal for giving a command regarding the driving amount of the end effector from the master control unit 21.

The image processing unit 23 processes the image signal obtained from the electronic camera (e.g., electronic endoscope) provided at the end of the slave arm 31, and generates an image signal to be displayed on the display unit 12, and then outputs the image signal to the display unit 12.

Figure 5:
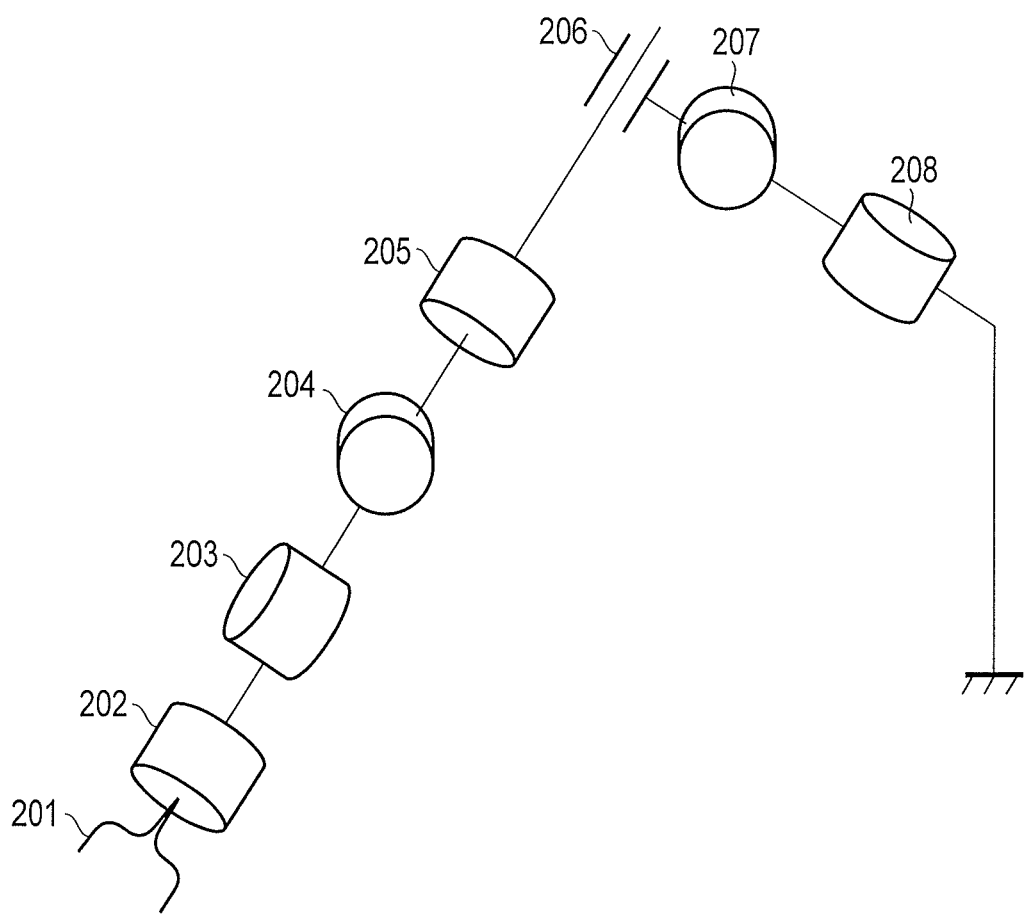
FIG. 5 is a diagram showing an example of the structure of a slave arm.

The slave manipulator 30 has the slave arm 31. Each joint of the slave arm 31 is driven in accordance with a control signal from the manipulator control unit 22. FIG. 5 shows an example of the structure of the slave arm 31. The slave arm 31 shown in FIG. 5 is provided with a series of seven joints 202 to 208. An end effector 201 is attached to the joint 202 at the distal end of the slave arm 31. Here, the joint at the distal end means a joint located farthest from the side where the slave arm 31 is fixed. The end effector 201 shown in FIG. 5 is an example of a gripper. A camera (e.g., electronic endoscope), for example, may be additionally attached to the end.

Among the joints shown in FIG. 5, the joints 202 and 205 are rolling joints that rotate around a rolling axis (corresponding to the X-axis shown in FIG. 2), the joints 203 and 208 are yawing joints that rotate around a yawing axis (corresponding to the Z-axis shown in FIG. 2), and the joints 204 and 207 are pitch joints that rotate around a pitch axis (corresponding to the Y-axis shown in FIG. 2). The joint 206 is a translation joint that translates along the rolling axis. In the example shown in FIG. 5, all the seven joints are independent of one another.

Three degrees of freedom in position and three degrees of freedom in orientation of the hand of the slave arm 31 are obtained by driving the joints 203 to 208 shown in FIG. 5 in cooperation with one another. In addition to these joints, the joint 202 for rolling the end effector 201 is provided as a redundant joint in FIG. 5. Such a configuration makes it possible to, for example, only roll the part in the vicinity of the end effector 201 in order to roll the slave arm 31. As described above, direct commands can be issued by the master operation input device 10 regarding the driving amounts of the joint 202 at the distal end and the end effector 201.

As described above, according to the present embodiment, the first rolling joint 102 which is an operation portion having the same structure as the joint 202 at the distal end of the slave arm 31 is provided in the position of the operation unit 11 of the master operation input device 10 where the operator 1 can operate the first rolling joint 102 with his/her fingertip while gripping the grip portion 101. This permits the operator 1 to stably operate the slave arm 31 having seven degrees of freedom with one hand.

Here, suturing is needed after surgery, for example, in endoscopic surgery. To this end, the gripper serving as the end effector 201 attached to the end of the slave arm 31 is rolled to suture a necessary part of a patient. In this case, if the rolling joint 205 distant from the end effector 201 is rolled, the end effector 201 is also rolled. On the other hand, other joints also move to a great extent so that the joint of the slave arm 31 may collide with, for example, a surrounding organ. Therefore, when rolling is principally needed as in the case of suturing, it is preferable to roll the rolling joint 202 at the distal end of the slave arm 31 in such a manner as to prevent unnecessarily movement of other joints. In the present embodiment, the first rolling joint 102 has the same structure as the joint 202 at the distal end of the slave arm 31, so that the operator 1 can intuitively recognize the relation between the operation amount of the first rolling joint 102 and the driving amounts of the rolling joint 202. Thus, the operator 1 can finely control the driving amounts of the joint 202 at the distal end of the slave arm 31. That is, the joint 202 at the distal end can be operated by moving the first rolling joint 102 while using the grip portion 101 gripped in the palm to indicate the position and orientation of the end effector 201. Accordingly, the orientation of the finger corresponds to the orientation of the end effector 201, thereby enabling intuitive operation. It should be understood that the orientation of the finger corresponds to the position and orientation of the end effector 201 even if the first rolling joint 102 does not rotate relative to the grip portion 101.

Furthermore, according to the present embodiment, since the end effector operation unit 103 is attached on the same straight line that connects the first rolling joint 102 with the grip portion 101, the operator 1 can operate the end effector operation unit 103 while gripping the grip portion 101. The first rolling joint 102 and the end effector operation unit 103 can be independently driven. $\theta_6$ can be acquired by putting a finger on the end effector operation unit 103 and thereby opening/closing the end effector operation unit 103. $\theta_5$ can be acquired by turning the end effector operation unit 103 and thereby rotating the first rolling joint 102 which is the base of the end effector operation unit 103.

The first rolling joint 102 according to the present embodiment is driven independently of other joints. Therefore, the master operation input device 10 according to the present embodiment is also applicable to the slave manipulator 30 that has six or less degrees of freedom without any redundant degree of freedom.

Modifications

Modifications of the embodiment are described below. First, in the example shown in FIG. 2, the first rolling joint 102 is supported by the grip portion 101 alone. Actually, the first rolling joint 102 has only to be configured to be able to roll independently of other joints. For example, as shown in FIG. 6, the first rolling joint 102 (the end effector operation unit 103 in FIG. 6) may be supported at two points including the grip portion 101 and the extension 101a. A schematic diagram of the configuration in FIG. 6 is shown in FIG. 7. As shown in FIG. 7, the first rolling joint 102 and the second rolling joint 104 are substantially adjacently arranged in the configuration shown in FIG. 6. In contrast, in a double-shaft structure in which the first rolling joint 102 and the second rolling joint 104 have different rotary shafts, the second rolling joint 104 does not roll in response to the rolling of the first rolling joint 102.

Figure 8A:
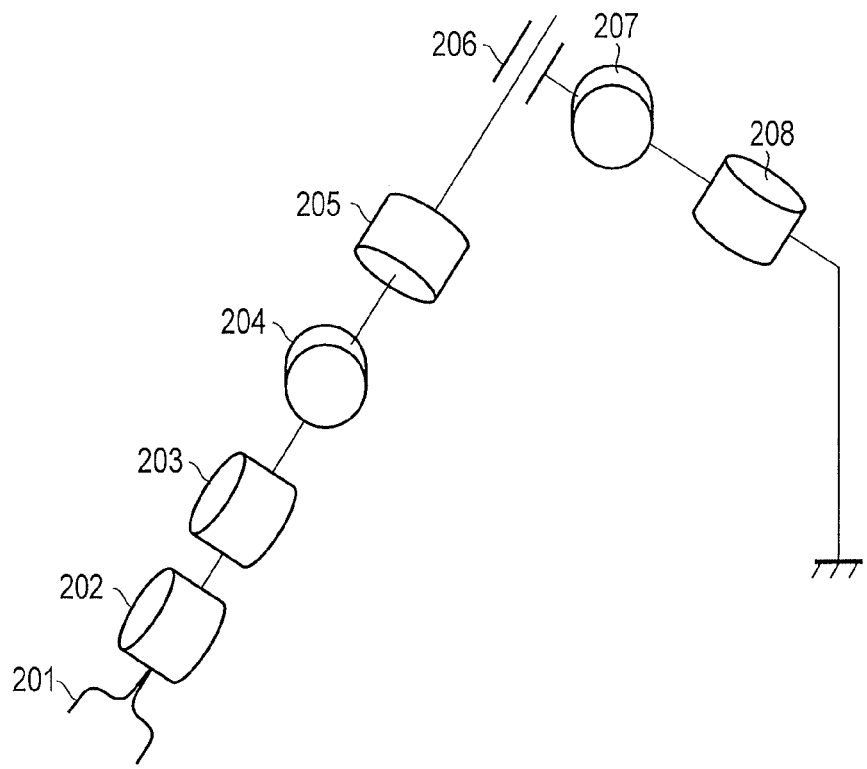
FIG. 8A is a diagram showing the structure of a slave arm according to a modification in which a joint provided in a grip portion is a yawing joint.
Figure 8B:
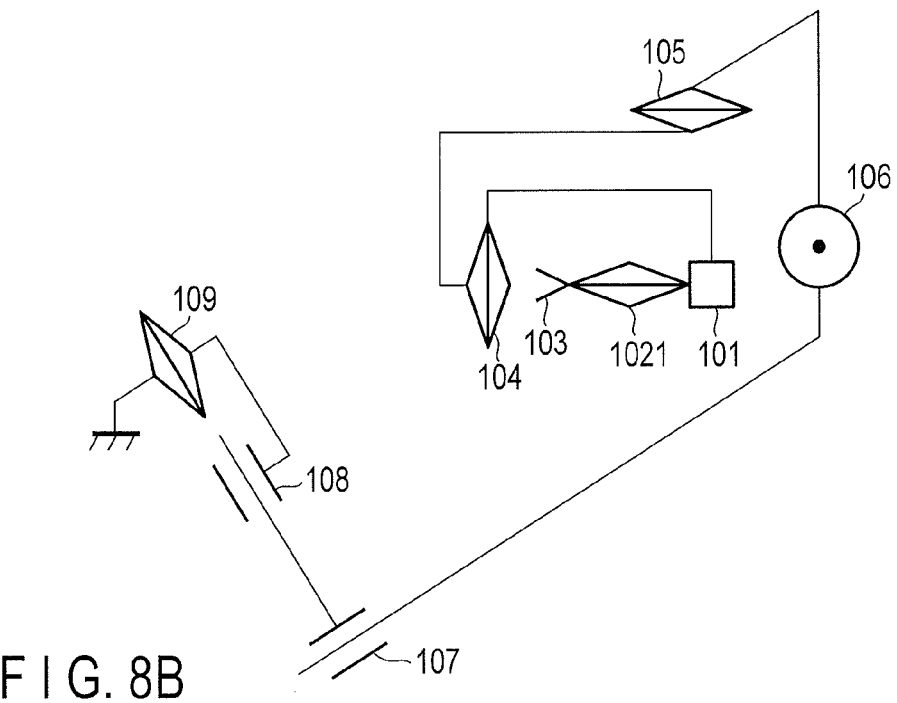
FIG. 8B is a diagram showing the structure of a master operation input device according to the modification in which the joint provided in the grip portion is a yawing joint.
Figure 9A:
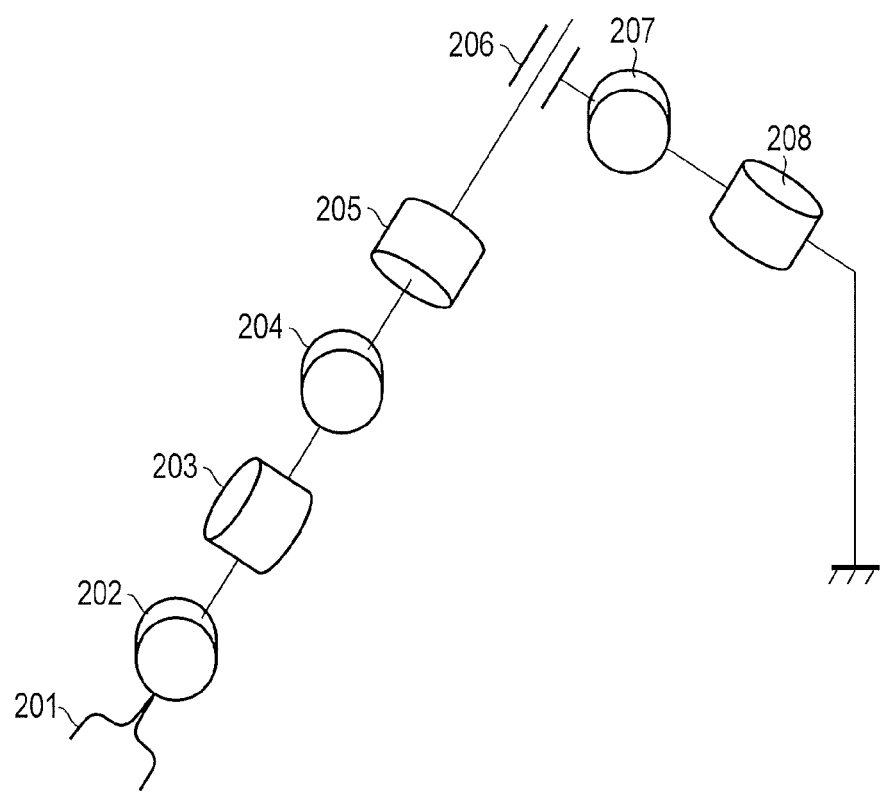
FIG. 9A is a diagram showing the structure of a slave arm according to a modification in which a joint provided in a grip portion is a pitch joint.
Figure 9B:
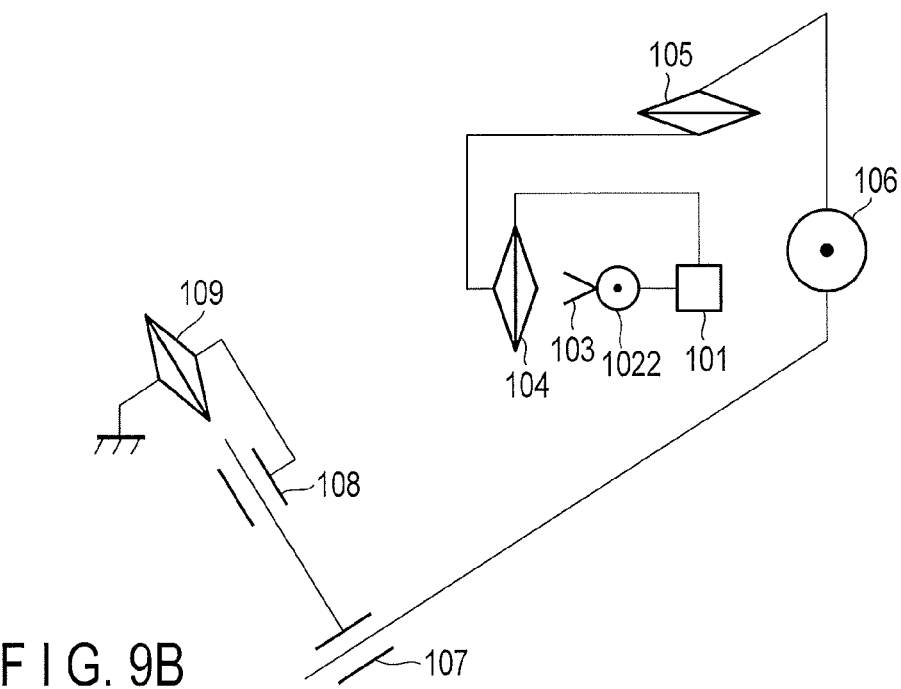
FIG. 9B is a diagram showing the structure of a master operation input device according to the modification in which the joint provided in the grip portion is a pitch joint.

In the example shown in FIG. 2, the grip portion 101 is provided with the rolling joint. This is attributed to that fact that the joint at the distal end of the slave arm 31 is a rolling joint. When the joint at the distal end of the slave arm 31 is not a rolling joint, the joint provided in the grip portion 101 is also changed. For example, when the joint at the distal end of the slave arm 31 is a yawing joint as shown in FIG. 8A, a joint 1021 provided in the grip portion 101 is also a yawing joint as shown in FIG. 8B. Similarly, when the joint at the distal end of the slave arm 31 is a pitch joint as shown in FIG. 9A, a joint 1022 provided in the grip portion 101 is also a pitch joint as shown in FIG. 9B. When the joint at the distal end of the slave arm 31 is a translation joint as shown in FIG. 10A, a joint 1023 provided in the grip portion 101 is also a translation joint as shown in FIG. 10B.

Figure 11A:
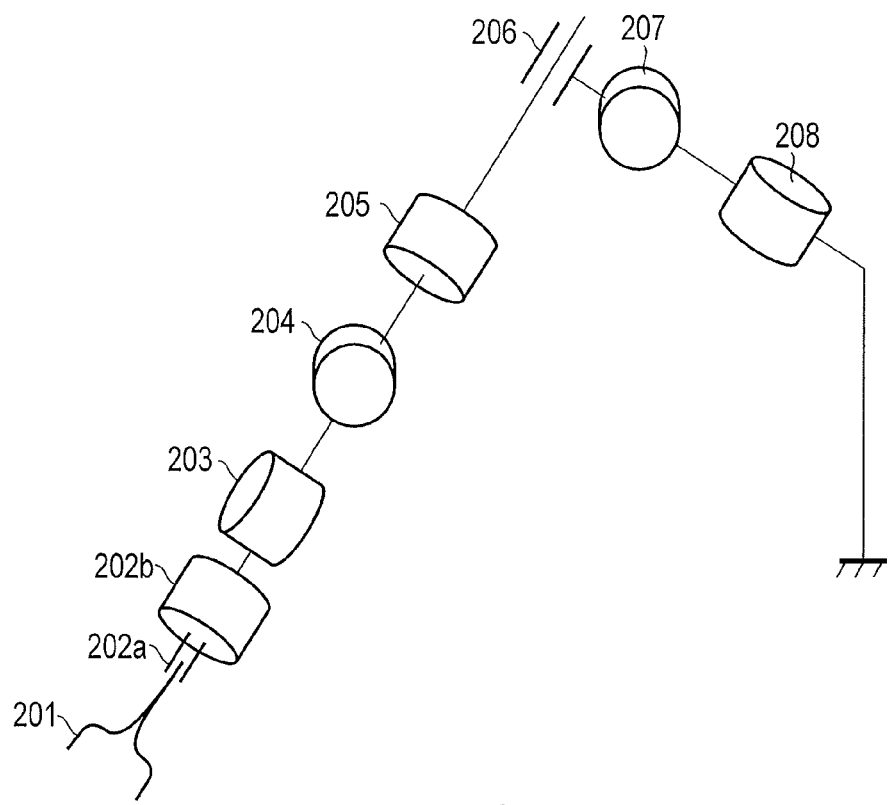
FIG. 11A is a diagram showing the structure of a slave arm according to a modification in which multiple joints are provided in a grip portion.
Figure 11B:
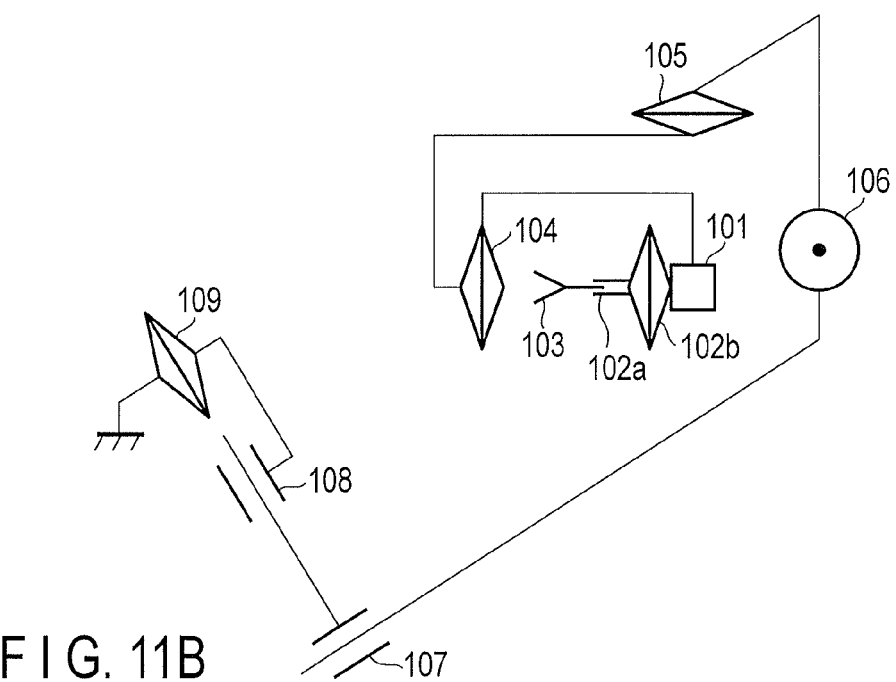
FIG. 11B is a diagram showing the structure of a master operation input device according to the modification in which the multiple joints are provided in the grip portion.

Moreover, when two or more kinds of independent joints 202a and 202b are provided at the distal end of the slave arm 31 as shown in FIG. 11A, more than one joint are provided in the grip portion 101. For example, FIG. 11A shows the slave arm 31 having eight degrees of freedom in which the rolling joint 202b and the translation joint 202a are added to the joints 203 to 208 corresponding to six degrees of freedom. In this case, the grip portion 101 is also provided with two joints including a rolling joint 102b and a translation joint 102a that can be independently operated. Such a configuration allows the joint at the distal end of the slave arm 31 to have the same structure as the joint provided in the grip portion 101. This enables the operator 1 to intuitively operate the rolling joint 202b and the translation joint 202a of the slave arm 31. Two joints are provided in the example shown in FIG. 11B. However, when the number of joints of the slave arm 31 is increased, the number of joints provided in the grip portion 101 of the master operation input device 10 is also increased accordingly.

When the structure of the end effector 201 of the slave arm 31 is different from the structure shown in FIG. 5, it is preferable to also change the structure of the end effector operation unit 103 accordingly.

Furthermore, the joints 104 to 109 provided in the operation unit 11 shown in FIG. 2 serve to give commands regarding the position and orientation of the end of the slave arm 31. The joints 104 to 109 may not be used as long as commands can be given regarding the position and orientation of the end of the slave arm 31. For example, if a sensor (e.g., an acceleration sensor) for detecting the translation of three axes is provided in the operation unit 11, the operation unit 11 can be configured as shown in FIG. 12. In the example shown in FIG. 12, if the operator 1 grips the grip portion 101 of the operation unit 11 to move or rotate the operation unit 11 in a three-dimensional space, operation signals corresponding to three degrees of freedom in position can be given. Operation signals corresponding to three degrees of freedom in orientation are obtained by analyzing the image obtained, for example, by a camera 13. FIG. 12 shows an example wherein the operation signal obtained by the operation unit 11 can be wirelessly communicated via a wireless communication unit 14. It should be understood that the operation signal obtained by the operation unit 11 may be communicated in a wired manner in the example shown in FIG. 12. The orientation of the operation unit 11 may be detected by an angular velocity sensor.

Hereinafter, several embodiments are described wherein the master-slave manipulator according to the above embodiment is combined with a predetermined form of control. In these embodiments, one of two joints that have a redundant relation in the slave arm 31 is set as a driven joint, and the other is used as a fixed joint. Thereby, the inverse-kinematic computation for obtaining the driving amount of each joint is simplified, and load on the manipulator control unit 22 is thus reduced. It is to be noted that in the present specification, "to have a redundant relation" means that operating axes such as the rotation axes or slide axes of the joints are parallel to each other.

In the first embodiment, an equivalent rotation vector (also referred to as an equivalent axis rotation vector or the like) is used to determine which joint to use as a driven joint. Thus, the equivalent rotation vector is explained.

Figure 13A:
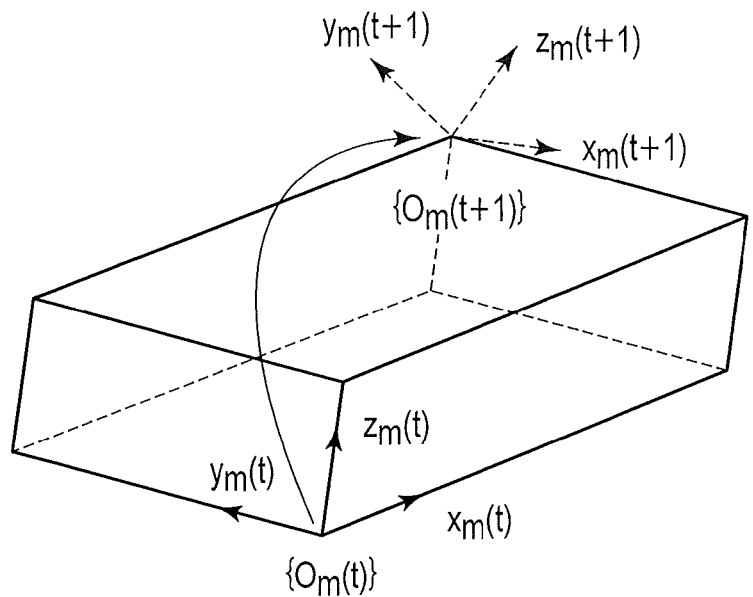
FIG. 13A is a diagram for explanation of move of an operation unit.
Figure 13B:
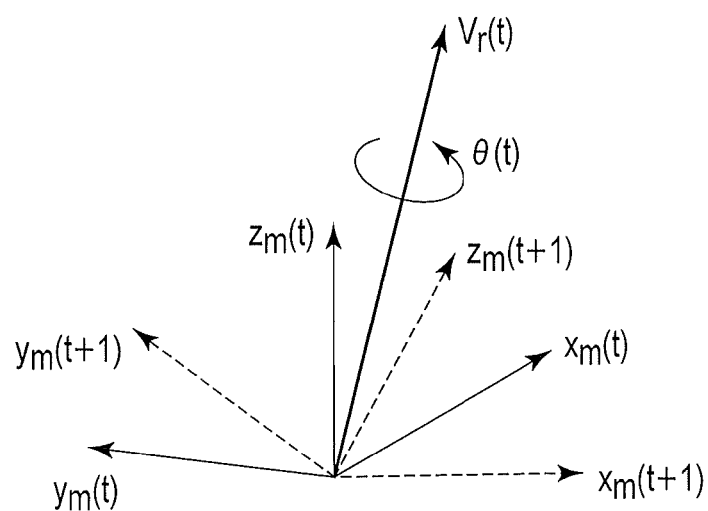
FIG. 13B is a diagram for explanation of move of an operation unit.

First, the orientation change of the grip portion 101 of the operation unit 11 is defined as follows. For example, at a given time t, the position of the grip portion 101 shown in FIG. 13C is a position Om(t) shown in FIG. 13A. The orientation of the grip portion 101 at the time t is an orientation such that a master roll axis Xm, a master pitch axis Ym, and a master yaw axis Zm are respectively in Xm(t), Ym(t), and Zm(t) directions shown in FIG. 13A and FIG. 13C. At a time t+1 after a given time Δt, the position of the grip portion 101 changes from the above state to a position Om(t+1) shown in FIG. 13A. The orientation of the grip portion 101 at a time t+1 changes to an orientation such that the master roll axis Xm, the master pitch axis Ym, and the master yaw axis Zm are respectively in Xm(t+1), Ym(t+1), and Zm(t+1) directions shown in FIG. 13A. The orientation change of the grip portion 101 at this point is the combination of the rotation around a master roll axis Xm(t), the rotation around a master pitch axis Ym(t), and the rotation around a master yaw axis Zm(t). Moreover, it is mathematically possible to replace the rotations around the three axes with the rotation around one axis. That is, as shown in FIG. 13B, if a given rotation axis Vr(t) is set, the orientation change of the grip portion 101 from the time t to the time t+1 is equivalent to a θ(t) rotation of the grip portion 101 around the rotation axis Vr(t). In general, a vector representing such a rotation axis Vr(t) is referred to as the equivalent rotation vector.

In the slave arm 31, the two roll joints 202 and 205 have a redundant relation, as shown in FIG. 5. In the first embodiment, the master control unit 21 sets one of the joints 202 and 205 as a driven joint, and sets the other joint as a fixed joint, in accordance with a determination that uses the above-mentioned rotation axis Vr. That is, at this point, the slave arm 31 is temporarily treated as having no redundant degree of freedom. It is therefore possible to easily perform the computation for obtaining the driving amount of each joint.

Figure 14:
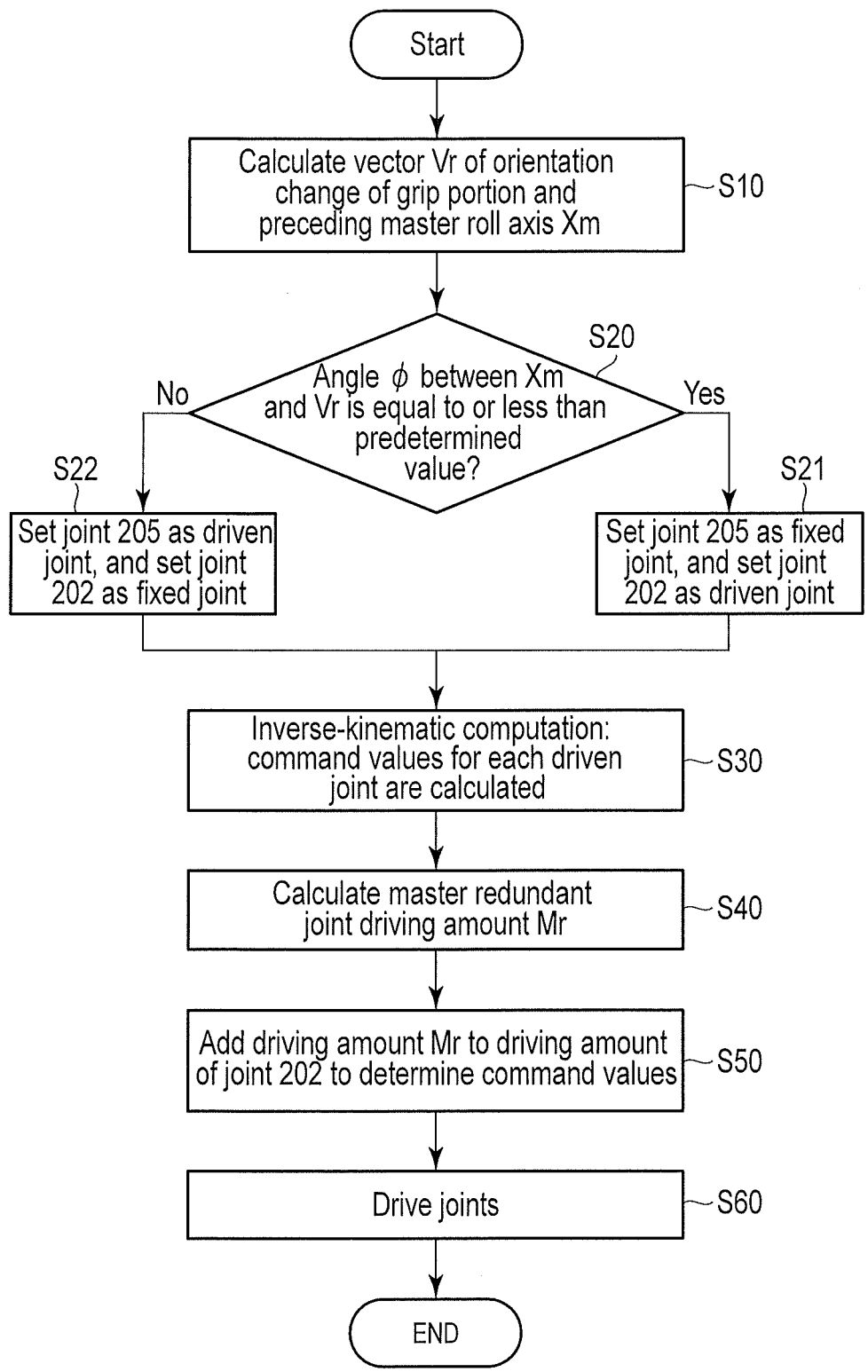
FIG. 14 is a flowchart showing the flow of the driving of joints of a slave arm in a first embodiment of the invention.

FIG. 14 is a flowchart showing the flow of the driving of the joints of the slave arm 31 in the first embodiment. In step S10, the master control unit 21 obtains the present position and orientation and the preceding position and orientation of the grip portion in accordance with an operation signal from the master operation input device 10. On the basis of these values, the master control unit 21 further calculates the preceding master roll axis Xm of the grip portion, and an equivalent rotation vector indicating the rotation axis Vr that results from the orientation change.

In step S20 that follows, the master control unit 21 determines whether an angle φ between the master roll axis Xm and the rotation axis Vr is equal to or less than a predetermined value that has been set in advance.

When the determination is Yes, the processing moves to step S21, and the master control unit 21 sets the joint 202 close to the end effector 201 as a driven joint, and sets the other joint 205 as a fixed joint. When, on the other hand, the determination is No, the processing moves to step S22, and the master control unit 21 sets the joint 205 far from the end effector 201 as a driven joint, and sets the other joint 202 as a fixed joint.

The determination in step S20 is based on the following concept.

That is, it can be thought that the orientation change of the grip portion 101 from the time t to the time t+1 is only attributed to the orientation change resulting from rolling if the equivalent rotation vector Vr(t) and the master roll axis Xm(t) correspond to each other (φ(t)=0). In this case, it can be thought that the operation unit 11 has given a command for the operation that only requires the rolling of the leading end of the slave arm 31. Actually, a predetermined value is set for an angle φ(t) between the equivalent rotation vector Vr(t) and the master roll axis Xm(t) in such a manner as to include not only the case where the equivalent rotation vector Vr(t) and the master roll axis Xm(t) completely correspond to each other but also the case where the operation mainly comprises the rolling of the leading end and also comprises other operations. When φ(t) is equal to or less than the predetermined value, the operation is considered to only comprise "small motion" such as suturing motion in which the distal roll axis joint is only operated. Therefore, the predetermined value to be a determining standard can be properly set depending on the degree of operation that is determined to be the "small motion". For example, the predetermined value can be 15 degrees.

After determining a driven joint and a fixed joint in step S21 or step S22, the master control unit 21 outputs a joint selection signal indicating the selection result to the manipulator control unit 22 together with command values regarding the position and orientation. After the end of step S21 or step S22, the processing moves to step S30.

In step S30, the manipulator control unit 22 uses the inverse-kinematic computation to calculate the driving amount of each joint of the slave arm 31 necessary for the position and orientation of the leading end of the slave arm 31 to correspond to command values, in accordance with the command values regarding the position and orientation received from the master control unit 21 and the joint selection signal. The manipulator control unit 22 thus determines the command values for each joint.

Here, the slave arm 31 originally has the joints corresponding to seven degrees of freedom. However, as one of the joints 202 and 205 that have a redundant relation is set as a fixed joint (i.e., set to a driving amount of zero), the number of joints to calculate the driving amounts by the inverse-kinematic computation can be smaller than when all the driving amounts of the seven degrees of freedom are unknown. Thus, the inverse-kinematic computation is simplified, and calculation load on the manipulator control unit 22 is reduced.

For the inverse-kinematic computation, various known techniques such as an analytic technique can be used. The details are not described here.

In step S40 that follows, the manipulator control unit 22 calculates a driving amount Mr of the first roll joint 102 which is a master-side redundant joint, in accordance with the information received from the master control unit 21.

Furthermore, in step S50, the manipulator control unit 22 adds the driving amount Mr calculated in step S40 to the driving amount of the joint 202 calculated in step S30, and determines command values for the joint 202. In consequence, command values for all the joints of the slave arm 31 are determined.

In step S60, the manipulator control unit drives the joints of the slave arm 31 in accordance with the command values for the joints of the slave arm 31 obtained in step S50, so that a series of processes is finished. This flow is repeated at predetermined intervals, for example, every ten to several ten milliseconds, and driven joints are repeatedly set.

For example, in endoscopic surgery, suturing motion is needed in putting in a suture after surgery. To this end, an end effector such as the gripper attached to the leading end of the slave arm is rolled to stitch a necessary part of a patient. The end effector is finely moved at the target part. As described above, the slave arm 31 cooperatively operates the seven joints to control the position and orientation of the end effector. If the joint far from the end effector (e.g., the joint 205) is rolled, for example, in the suturing motion, the end effector is also rolled. At the same time, the other joints are also operated to a great extent so that the joints of the slave arm 31 may collide with, for example, the surrounding organs.

In the first embodiment, when the angle $\phi$ is determined to be equal to or less than the predetermined value in step S20, the joint 202 close to the end effector 201 is set as a driven joint, and the joint 205 far from the end effector 201 is fixed. Therefore, in "small motion" such as suturing motion in which the end effector is only rolled, the other joints of the slave arm are not moved to a great extent, and procedures and operations with small motion can be more safely performed on a patient.

As one of the joints 202 and 205 that have a redundant relation is set as a fixed joint, the inverse-kinematic computation in step S30 can be simplified. As a result, load imposed on the manipulator control unit by the calculation is reduced, and the time required for the calculation is reduced, so that the joints of the slave arm can be smoothly driven.

Now, the second embodiment is described below.

The second embodiment only differs in the determining standard for the selection of the driven joint. Therefore, the determining standard is mainly described, and like parts are not repeatedly explained.

Figure 15:
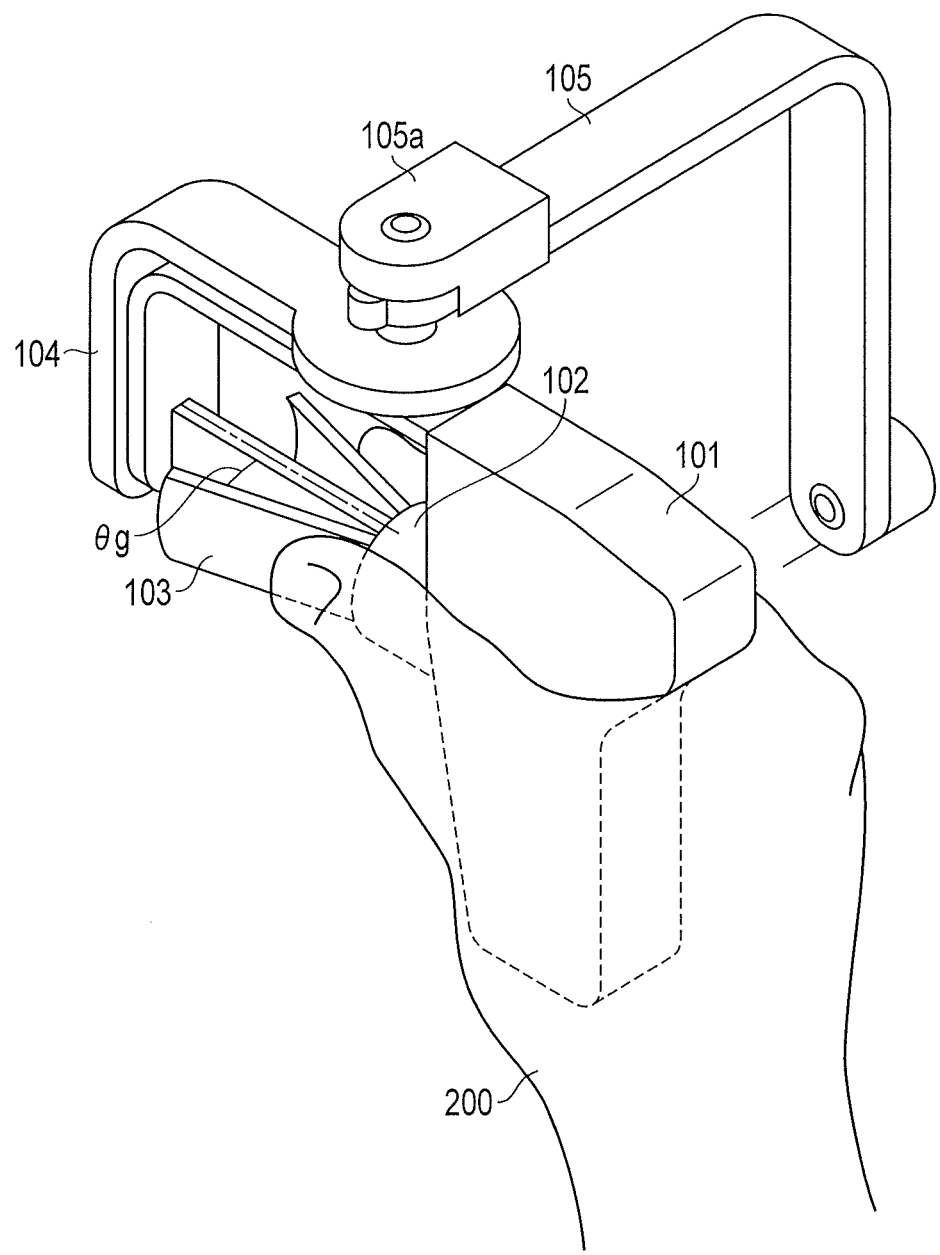
FIG. 15 is a diagram showing an opening angle of the end effector operation unit.

In the second embodiment, when the end effector operation unit 103 is closed, something is gripped by the end effector 201, that is, the above-mentioned "small motion" is performed. On the basis of this concept, a determination is made to select a driven joint in accordance with the value of the opening angle $\theta g$ of the end effector operation unit 103 shown in FIG. 15.

FIG. 16 is a flowchart showing the flow of the driving of the joints of the slave arm 31 in the second embodiment. In step S10A, the opening angle $\theta g$ of the end effector operation unit 103 is measured, and sent to the master control unit 21 from the master operation input device 10. In step S20A, the master control unit 21 determines whether the opening angle $\theta g$ is equal to or less than a predetermined value, for example, one degree.

When the determination in step S20A is Yes, the processing moves to step S21, and the master control unit 21 sets the joint 202 close to the end effector 201 as a driven joint, and sets the other joint 205 as a fixed joint. When, on the other hand, the determination is No, the processing moves to step S22, and the master control unit 21 sets the joint 205 far from the end effector 201 as a driven joint, and sets the other joint 202 as a fixed joint.

The subsequent flow is similar to that in the first embodiment.

In the second embodiment, when, for example, a needle is gripped by the end effector 201, the value of the opening angle $\theta g$ is equal to or less than the predetermined value, and the joint 202 is set as a driven joint. Therefore, as in the first embodiment, in "small motion", the other joints of the slave arm are not moved to a great extent, and procedures and operations with small motion can be more safely performed on a patient.

In the example described in the second embodiment, the value of the opening angle $\theta g$ is acquired from the master operation input device 10. Alternatively, an angle sensor, for example, may be provided in the end effector 201, and the opening angle of the end effector 201 may be acquired and used for the determination in step S20A. When the opening angle of the end effector 201 is used for the determination in step S20A, an image of the end effector displayed on the display unit may be processed to acquire the opening angle of the end effector 201.

Now, the third embodiment is described below.

The third embodiment only differs from the first embodiment in the determining standard for the selection of the driven joint. Therefore, the determining standard is mainly described, and like parts are not repeatedly explained.

Figure 17:
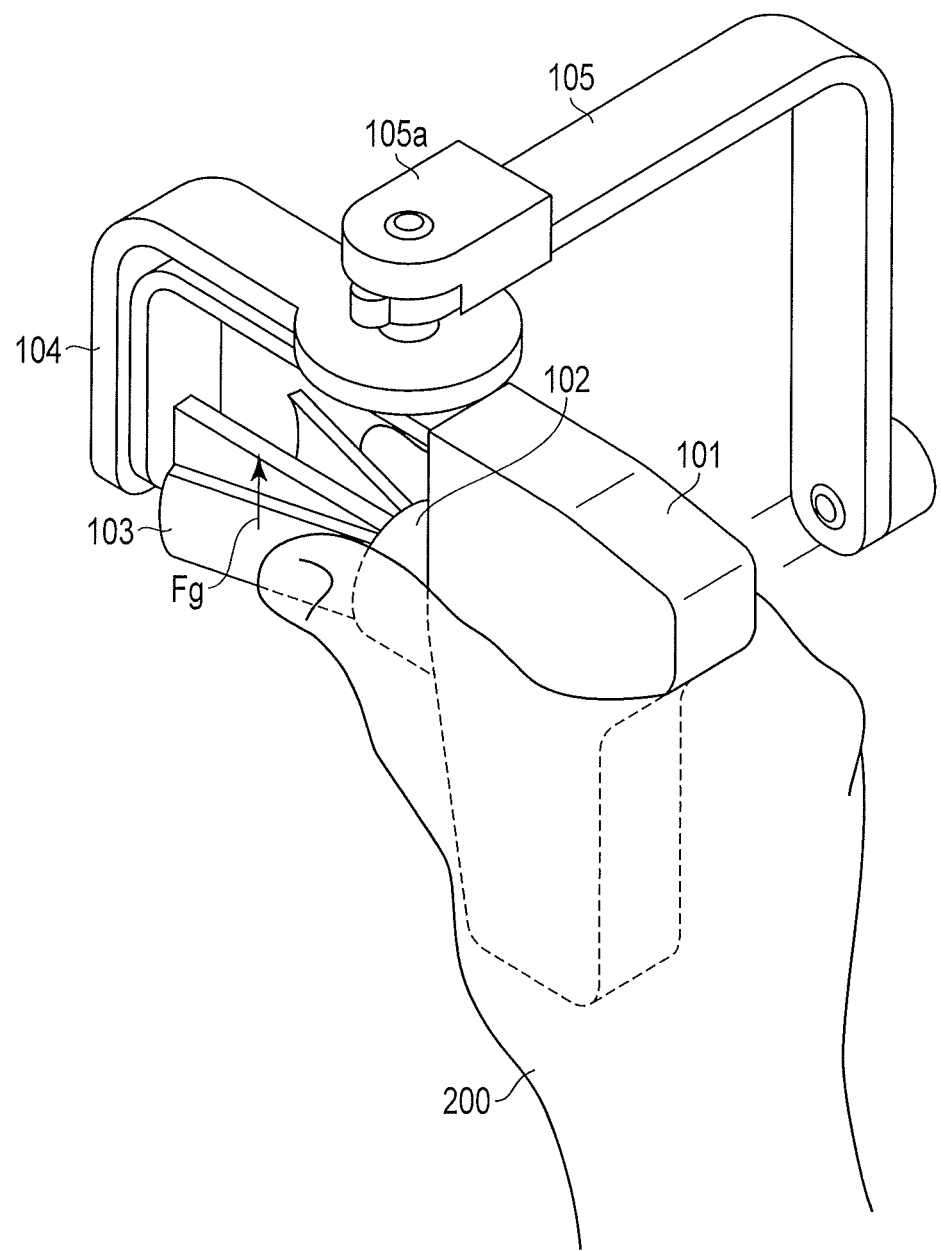
FIG. 17 is a diagram showing force acting on the end effector operation unit.

In the third embodiment, when force equal to or more than a predetermined value is acting on the end effector operation unit 103, something is gripped by the end effector, that is, the above-mentioned "small motion" is performed. On the basis of this concept, a determination is made to select a driven joint in accordance with the value of the force Fg acting on the end effector operation unit 103 shown in FIG. 17. In the third embodiment, a known force sensor, for example, is attached to the end effector operation unit 103 so that the force Fg can be detected, and the detection value is sent to the master control unit 21.

FIG. 18 is a flowchart showing the flow of the driving of the joints of the slave arm 31 in the third embodiment. In step S10B, the force Fg acting on the end effector operation unit 103 is measured, and sent to the master control unit 21 from the master operation input device 10. In step S20B, the master control unit 21 determines whether the force Fg is equal to or more than a predetermined value, for example, 1 N.

When the determination in step S20B is Yes, the processing moves to step S21, and the master control unit 21 sets the joint 202 close to the end effector 201 as a driven joint, and sets the other joint 205 as a fixed joint. When, on the other hand, the determination is No, the processing moves to step S22, and the master control unit 21 sets the joint 205 far from the end effector 201 as a driven joint, and sets the other joint 202 as a fixed joint.

The subsequent flow is similar to that in the first embodiment.

In the third embodiment, when, for example, a needle is gripped by the end effector 201, the value of the force Fg is equal to or more than the predetermined value, and the joint 202 is set as a driven joint. Therefore, as in the first embodiment, in "small motion", the other joints of the slave arm are not moved to a great extent, and procedures and operations with small motion can be more safely performed on a patient.

In the example described in the third embodiment, the value of the force Fg is acquired from the master operation input device 10. Alternatively, a force sensor, for example, may be provided in the end effector 201, and the value of reactive force applied to the end effector 201 by the gripping of, for example, a needle may be acquired and used for the determination in step S20B.

Now, the fourth embodiment is described below.

The fourth embodiment only differs from the first embodiment in the determining standard for the selection of the driven joint. Therefore, the determining standard is mainly described, and like parts are not repeatedly explained.

In the fourth embodiment, when the grip portion 101 of the master operation input device 10 is moving at a relatively high speed, the end effector 201 is being moved to a part to be treated, that is, the above-mentioned "small motion" is not performed. On the basis of this concept, a determination is made to select a driven joint in accordance with the movement amount of the grip portion 101.

Figure 19:
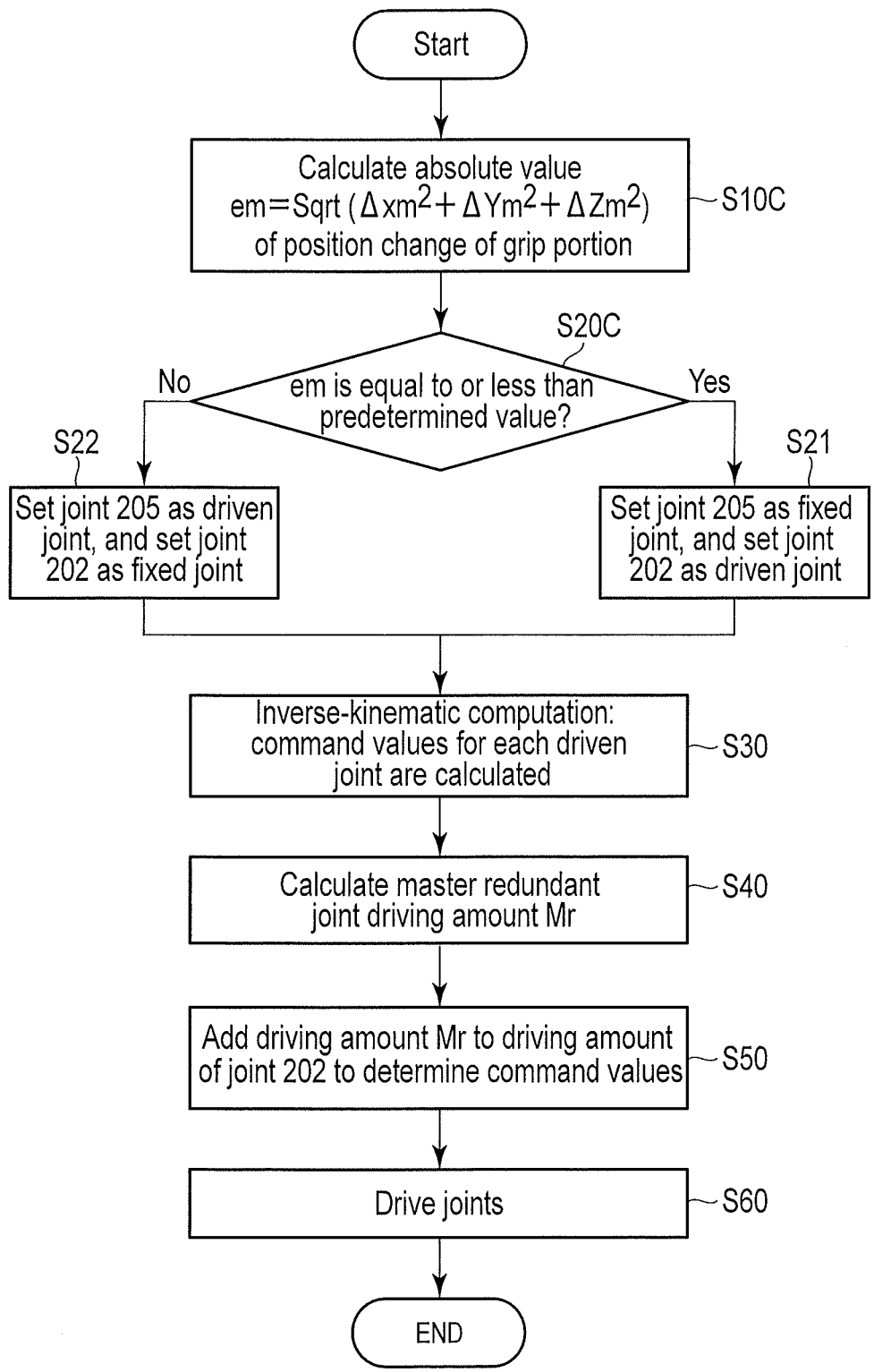
FIG. 19 is a flowchart showing the flow of the driving of the joints of the slave arm in a fourth embodiment of the invention.

FIG. 19 is a flowchart showing the flow of the driving of the joints of the slave arm 31 in the fourth embodiment. In step S10C, the master control unit 21 obtains the current position and the preceding position of the grip portion 101 in accordance with an operation signal from the master operation input device 10. On the basis of these values, the master control unit 21 then acquires an absolute value em (the square root of $(\Delta Xm^2+\Delta Ym^2+\Delta Zm^2)$) of the position change of the grip portion 101.

In step S20C that follows, the master control unit 21 determines whether the absolute value em is equal to or less than a preset value. When the determination is Yes, this means that the movement amount of the grip portion 101 in a predetermined interval is small, that is, the grip portion 101 is moving at a relatively low speed. Thus, the processing moves to step S21, and the joint 202 close to the end effector 201 is set as a driven joint, and the other joint 205 is set as a fixed joint. When, on the other hand, the determination is No, the processing moves to step S22, and the master control unit 21 sets the joint 205 far from the end effector 201 as a driven joint, and sets the other joint 202 as a fixed joint.

The subsequent flow is similar to that in the first embodiment.

In the fourth embodiment, in "small motion", the other joints of the slave arm are not moved to a great extent, and procedures and operations with small motion can be more safely performed on a patient, as in the first embodiment.

In the example described in the fourth embodiment, the movement amount of the grip portion is acquired from the master operation input device. Alternatively, the movement amount of the end effector provided at the distal end of the slave arm may be acquired and used for the determination in step S20C.

While the present invention has been described above in connection with the embodiments, the present invention is not limited to the embodiments described above. It should be understood that various modifications and applications can be made within the spirit of the present invention.

Furthermore, the embodiments described above include various stages of inventions, and various inventions can be extracted by properly combining the disclosed features. For example, when the above-mentioned problems can be solved and the above-mentioned advantages can be obtained even if some of all the features shown in the embodiments are eliminated, a configuration in which those features are eliminated can also be extracted as an invention.

For example, in the examples described above according to the embodiments, the roll joints 202 and 205 have a redundant relation in the slave arm. However, the form of control described above is also applicable to the case where joints that have a redundant relation are not roll joints. Therefore, joints that have a redundant relation may be the yaw joints 202 and 208 shown in FIG. 8A, or may be the pitch joints 202 and 204 shown in FIG. 9A. Alternatively, joints that have a redundant relation may be the slide joints 202 and 206 shown in FIG. 10A.

What is claimed is:

1. A master operation input device to operate a slave manipulator provided with joints adapted to multiple degrees of freedom, the master operation input device comprising:
    a grip portion which is variable in position and orientation while being gripped by an operator, the grip portion being configured to give command values regarding the position and orientation of a distal end of the slave manipulator in accordance with the variation in position and orientation, the distal end being the farthest end when the slave manipulator is viewed from a fixed end thereof;
    a first operation portion to operate at least one of the joints of the slave manipulator, the first operation portion being operable independently of the grip portion; and
    a second operation portion to operate an effector provided in the joint at the distal end of the slave manipulator, the second operation portion being attached to the first operation portion, the second operation being operable independently of the first operation portion,
    wherein each of the first operation portion and the second operation portion is located to be operable by a fingertip of the operator when the grip portion is gripped.

2. The master operation input device according to claim 1, wherein the first operation portion has the same structure as a joint at the distal end of the slave manipulator regarding the grip portion, and the first operation portion is configured to give a command value regarding a driving amount to drive the joint at the distal end of the slave manipulator in response to a manual operation.

3. The master operation input device according to claim 1, wherein the grip portion, the first operation portion, and the second operation portion are collinear.

4. The master operation input device according to claim 1, wherein the first operation portion is supported by the grip portion.

5. The master operation input device according to claim 4, wherein the grip portion is attached to an arm portion which is driven in accordance with the variation in position and orientation of the grip portion.

6. The master operation input device according to claim 5, wherein the first operation portion is further supported by the arm portion.

7. The master operation input device according to claim 1, wherein the joint at the distal end of the slave manipulator comprises joints adapted to multiple degrees of freedom, and the first operation portion is configured to give command values regarding driving amounts of the joints provided the joint at the distal end of the slave manipulator.

8. A master-slave manipulator comprising:
    a slave manipulator provided with joints adapted to multiple degrees of freedom;
    a master operation input device to operate the slave manipulator; and a control unit configured to calculate a driving amount of each joint of the slave manipulator from the command values regarding the position and orientation and from a command value regarding a driving amount to drive the joint at the distal end of the slave manipulator, the control unit driving each joint of the slave manipulator in accordance with a calculation result of the driving amount, wherein the master operation input device comprising:
- a grip portion which is variable in position and orientation while being gripped by an operator, the grip portion being configured to give command values regarding the position and orientation of a distal end of the slave manipulator in accordance with the variation in position and orientation, the distal end being the farthest end when the slave manipulator is viewed from a fixed end thereof;
- a first operation portion to operate at least one of the joints of the slave manipulator, the first operation portion being operable independently of the grip portion; and
- a second operation portion to operate an effector provided in the joint at the distal end of the slave manipulator, the second operation portion being attached to the first operation portion, the second operation being operable independently of the first operation portion, and wherein each of the first operation portion and the second operation portion is located to be operable by a fingertip of the operator when the grip portion is gripped.

9. The master-slave manipulator according to claim 8, wherein the first operation portion has the same structure as a joint at the distal end of the slave manipulator regarding the grip portion, and the first operation portion is configured to give a command value regarding a driving amount to drive the joint at the distal end of the slave manipulator in response to a manual operation.

10. The master-slave manipulator according to claim 8, wherein the grip portion, the first operation portion, and the second operation portion are collinear.

11. The master-slave manipulator according to claim 8, wherein the first operation portion is supported by the grip portion.

12. The master-slave manipulator according to claim 11, wherein the grip portion is attached to an arm portion which is driven in accordance with the variation in position and orientation of the grip portion.

13. The master-slave manipulator according to claim 12, wherein the first operation portion is further supported by the arm portion.

14. The master-slave manipulator according to claim 8, wherein the joint at the distal end of the slave manipulator comprises joints adapted to multiple degrees of freedom, and the first operation portion is configured to give command values regarding driving amounts of the joints provided at the joint at the distal end of the slave manipulator.

* * * * *